United States Patent
Yeung et al.

(10) Patent No.: US 7,674,607 B2
(45) Date of Patent: Mar. 9, 2010

(54) DNA ENCODING G+C-RICH PROMOTER BINDING PROTEIN

(75) Inventors: Cho-Yau Yeung, Oak Park, IL (US); Li-Chung Hsu, San Diego, CA (US); Shu Liu, Chicago, IL (US)

(73) Assignee: Munin Corporation, Chicago, IL (US)

( * ) Notice: Subject to any disclaimer, the term of this patent is extended or adjusted under 35 U.S.C. 154(b) by 0 days.

(21) Appl. No.: 12/112,904

(22) Filed: Apr. 30, 2008

(65) Prior Publication Data

US 2009/0011500 A1   Jan. 8, 2009

Related U.S. Application Data

(60) Division of application No. 10/947,997, filed on Sep. 22, 2004, now Pat. No. 7,368,538, which is a continuation-in-part of application No. PCT/US03/07870, filed on Mar. 17, 2003.

(60) Provisional application No. 60/366,898, filed on Mar. 22, 2002.

(51) Int. Cl.
*C12P 21/06* (2006.01)
*C12N 15/00* (2006.01)
*C12N 5/00* (2006.01)
*C07H 21/04* (2006.01)
*C07K 1/00* (2006.01)

(52) U.S. Cl. .................. 435/69.1; 435/320.1; 435/325; 536/23.1; 536/23.5; 530/350

(58) Field of Classification Search ....................... None
See application file for complete search history.

(56) References Cited

U.S. PATENT DOCUMENTS 5,580,703 A   12/1996   Kotin et al.

FOREIGN PATENT DOCUMENTS

WO   WO 00/58473   10/2000

OTHER PUBLICATIONS

International Search Report of PCT/US03/07870 dated Jan. 6, 2005.
Kudo, S., Methyl-CpG-Binding Protein MeCP2 Represses Sp1-Activated Transcription of the Human Leukosialin Gene When the Promoter is Methylated, Molecular and Cellular Biology, vol. 18, No. 9, pp. 5492-5499 (1998).

*Primary Examiner*—Olga N Chernyshev
(74) *Attorney, Agent, or Firm*—Howrey LLP

(57) ABSTRACT

A novel transcription regulator of G+C-rich promoters, the murine G+C-rich Promoter Binding Protein (mGPBP), and its interaction pattern with other transcription factors are disclosed. A human homologue of mGPBP, hGPBP, is described as well.

6 Claims, 11 Drawing Sheets

Figure 1A

```
CTAGAATTCAGCGGCCGCTGAATTCTAGAATGAGACTGGTTGTGGGGGAGGGAAAAGCGGCAAAAGGGGATTATTCAAAGTACC
GAAAACCTCCTCCCGGGATCGAGCGCAGCGGCACCCCCAGGCCAGGGGCACCTCTGGTGGGGCAGAAGGTGGTTGAATTTGGCG
TATGAAGATCATCATCTAGGTTTTGTTTAAAAGGCCCCGGATATTTCAAGTGGCCATTTTGGAATTACAGTTTTGTTTTTGTTT
TGGGCAATTTTGCTCCAGAAGTTCATTAAAATTGACAAGAATCATCTCTGAAGTGAATTGATAGTAGTGAACAAATTCAACGAG
CTACTAAAAGTCCCAGCCATTTCTTCAGTATTTTGGGTCAAACGGATTATATAAGTGGTTAAAGCATTTCATCTGGTGTTATTT
TTGTCTCTTTCCCCTCTCCTGTTTGTGTTCTTCAGCCAAAACTGTAAGATATGTTTGATTTGTGTACCAAGTAGTTTCAGCAGT
TTCAAATTACTGTTTAAATATTGCTGAAGTTTTGTGGCAGTTCTTTTTACCTTTATTAAAAGTTTTAGTAATTTTTGACTTCAG
CTTTTTTCATATTACAATGGGACAGCTTTTCTAAATGAAGACATTGAAAGAATACAGCGTTTTTTTCTTTTTATCTTTTATTTA
CTTGGGAATGTAAGATGTTCCATTTTCACACCAGCATGGTAGTATTGAGATAGCTATTTGTCTATACACGCTGATGTTTAGAAG
TAATCTTCAGATGTGAAATTTTTCTTTTTGTTTCTGCTTTTTGGCACATAAATTGGCTATTTCTTCTGGAGTGGATAAGTACAA
CAGTGACAAATACATGGAACAGTAAAGAAGACCTTGCTCTTAAATCCAAGGAACCTGGCTAACTCTGGATCTGACCATATGAAA
ACTTCAAAGTAAATATGGGTAGCTGACTTCAAGTAACTCTATGTCAAATAGTCATAGGTTAAGTATCTTCAAAGAACTTGGATA
TTTCAGAGGATACAAAATAAAAAAACAAACTGGAAAACATAAAGCTTATAGAGAAGAAATCAACACCTTCTTGTGCAGTCCTTT
                                                                   Met Ala Gln His Asp
TGGAATTTGGACTTGCCATGAGGTGTTGAAGCCTTGTTTCACTGAGTTGGAGAGACTGGACCTAAATG GCG CAG CAT GAC
Phe Ala Pro Ala Trp Leu Asn Phe Pro Thr Pro Pro Ser Ser Thr Lys Ser Ser Leu Asn Phe
TTT GCT CCA GCC TGG CTT AAT TTT CCT ACT CCT CCA TCA TCA ACA AAG TCA TCA TTG AAT TTT
Glu Lys His Ser Glu Asn Phe Ser Trp Thr Glu Asn Arg Tyr Asp Val Ser Arg Arg Arg His
GAG AAG CAC TCT GAA AAT TTT TCA TGG ACA GAA AAT CGT TAT GAT GTG AGT CGT CGA CGA CAC
Asn Ser Ser Asp Gly Phe Asp Ser Gly Ile Gly Arg Pro Asn Gly Gly Asn Phe Gly Arg Lys
AAT TCT TCA GAT GGC TTT GAT TCT GGT ATT GGA CGT CCT AAT GGA GGT AAT TTT GGG AGG AAA
Glu Lys Asn Gly Trp Arg Thr His Gly Arg Asn Gly Thr Glu Asn Ile Asn His Arg Gly Gly
GAG AAA AAT GGA TGG CGT ACG CAT GGC AGA AAT GGT ACA GAA AAC ATA AAT CAT CGT GGG GGA
Tyr His Gly Gly Asn Ser Arg Ser Arg Ser Ser Ile Phe His Ser Gly Lys Ser Gln Gly Leu
TAC CAT GGT GGA AAT TCC CGT TCT CGT AGC AGT ATT TTC CAT TCT GGA AAA AGC CAA GGA CTA
His Glu Asn Ser Ile Pro Asp Asn Glu Thr Gly Arg Lys Glu Asp Lys Arg Glu Arg Arg Gln
CAT GAA AAC AGC ATC CCT GAC AAT GAA ACT GGG AGG AAA GAA GAC AAA AGA GAA CGC AGA CAG
Phe Glu Ala Glu Asp Phe Pro Ser Leu Asn Pro Glu Tyr Glu Arg Glu Pro Asn Gln Asn Lys
TTT GAG GCT GAG GAT TTT CCA TCT TTA AAT CCT GAA TAT GAG AGA GAA CCA AAT CAG AAT AAA
Ser Leu Ala Ala Gly Val Trp Gly Leu His Ala Gln Thr His Thr Tyr Pro Thr Lys Lys Ile
TCT TTA GCT GCG GGT GTT TGG GGC CTA CAC GCC CAG ACA CAC ACA TAC CCA ACC AAA AAA ATC
Ser Gln Ala Pro Leu Leu Asp Tyr Pro Pro Asn Pro Lys Ser Arg Thr Pro Arg Met Leu Val
TCC CAA GCT CCT CTC TTA GAC TAT CCC CCG AAT CCT AAA TCT AGA ACT CCA AGA ATG CTG GTC
Ile Lys Lys Gly Asn Thr Lys Asp Leu Gln Leu Ser Gly Phe Pro Val Ala Gly Asn Leu Gln
ATT AAG AAA GGT AAT ACA AAA GAC TTA CAG CTA TCT GGA TTC CCA GTA GCA GGA AAC CTC CAG
Ser Gln Pro Val Lys Asn Gly Thr Ser Pro Ser Val Tyr Lys Gly Leu Val Pro Lys Pro Ala
TCA CAG CCA GTT AAG AAT GGA ACT AGT CCA AGT GTT TAT AAA GGC TTA GTC CCC AAA CCT GCT
Val Pro Pro Thr Lys Pro Thr Gln Trp Lys Ser Gln Thr Lys Glu Asn Lys Val Gly Thr Ser
GTT CCA CCT ACA AAA CCT ACA CAA TGG AAA AGC CAA ACT AAA GAA AAC AAA GTC GGG ACT TCT
Phe Ser His Glu Ser Thr Tyr Gly Val Gly Asn Phe Asn Thr Phe Lys Ser Thr Ala Lys Asn
TTT TCT CAT GAA TCT ACA TAT GGT GTT GGC AAC TTT AAT ACT TTT AAG TCA ACG GCC AAG AAT
Ile Ser Pro Ser Thr Asn Ser Val Lys Glu Cys Asn Arg Ser Asn Ser Ser Ser Pro Val Asp
ATT AGT CCA TCA ACA AAT TCA GTG AAA GAG TGT AAT CGT TCA AAT TCT TCT TCG CCT GTT GAC
Lys Leu Asn Gln Gln Pro Arg Leu Thr Lys Leu Thr Arg Met Arg Ser Asp Lys Lys Ser Glu
AAA CTT AAT CAG CAG CCT CGT TTA ACT AAA CTG ACA CGA ATG CGC AGC GAT AAA AAG AGT GAA
Phe Leu Lys Ala Leu Lys Arg Asp Arg Val Glu Glu Glu His Glu Asp Glu Ser His Ala Gly
TTT TTG AAA GCA TTG AAA AGG GAC AGA GTG GAG GAG CAT GAA GAT GAA GAT CAT GCT GGC
Ser Glu Lys Asp Asp Asp Ser Phe Asn Leu His Asn Ser Asn Thr Thr His Gln Glu Arg Asp
TCA GAG AAG GAC GAC GAC TCA TTT AAT TTG CAT AAC AGC AAT ACT ACT CAC CAA GAA AGA GAT
Ile Asn Arg Asn Phe Asp Glu Asn Glu Ile Pro Gln Glu Asn Gly Asn Ala Ser Ile Ile Ser
ATA AAC AGA AAC TTT GAT GAA AAT GAA ATT CCA CAG GAG AAC GGC AAT GCC TCG ATA ATT TCT
Gln Gln Ile Ile Arg Ser Ser Thr Phe Pro Gln Thr Asp Val Leu Ser Ser Ser Leu Glu Ala
CAA CAG ATC ATT CGT TCT TCA ACT TTT CCA CAA ACT GAT GTT CTT TCC AGT TCA CTA GAG GCA
Glu His Arg Leu Leu Lys Glu Met Gly Trp Gln Glu Asp Ser Glu Asn Asp Glu Thr Cys Ala
GAA CAC AGA TTA TTA AAA GAA ATG GGC TGG CAG GAA GAC AGT GAA AAT GAT GAA ACA TGT GCT
Pro Leu Thr Glu Asp Glu Met Arg Glu Gln Val Ile Ser Glu Gln Leu Gln Lys Asn Gly
CCC TTA ACT GAG GAT GAA ATG AGA GAA TTC CAA GTT ATT AGT GAA CAG TTA CAG AAG AAT GGT
Leu Arg Lys Asn Gly Ile Leu Lys Asn Gly Leu Ile Cys Asp Phe Lys Phe Gly Pro Trp Lys
CTG AGA AAA AAT GGT ATT TTG AAA AAT GGC CTG ATC TGT GAC TTC AAG TTT GGA CCC TGG AAA
Asn Ser Thr Phe Lys Pro Thr Ile Glu Asn Asp Asp Thr Glu Thr Ser Ser Ser Asp Thr Ser
AAC AGC ACT TTC AAA CCC ACA ATT GAG AAT GAT GAC ACA GAG ACA AGT AGC AGC GAC ACG TCG
Asp Asp Asp Asp Val
GAT GAT GAC GAT GTG TGAAGGAGATCCTCACAGCTTTAGAAATGTTAGTGTGATACATCTCTCATGCAGTTTGGGGTG
ATTGTAAAAATGAAGAACTATAATTTATGTAGTGAACCTACCCCATTAGAAGATGATTTTTTGGGGGACTTCGATATGAAGAA
AACCAAGAATGTTGTGTTGGGCTGTGTTGAACATTATTTCTTTGTAAATGAATGTTGTAGAAATGAGGACTTTGGTTGATCCA
ACATTGACTTTCTTCATCACTGCAGCATTTCTCTTGACTAGCAATGTGACGATGTAACAAATGAGATTTTCTCATTTAATAAT
AAAAAATTGTGTGATGTTTTGCAAAGCTTCTGTCTTAAATGTTCAGGTCTTAAGGTACAAGGCAGCTTACAGTTTTGCTTGC
AGAGTCCTATCTTTTTCAAACTGTGGAAATCTTCAACTCTACGTGTGCACCTCCTTATCCACTCCCCCTAAAACAAAACAACA
GCAAAAAGGAAATGTAGCATGTTGGCTAAAACCGGAGCAGAGTGACTAAAACATTAGCTTCTTGAACTCAACTCTTGTACTA
AGTCACCTTTCCAAACAAATTCCTCTTTAGTCTTTGGTAGCAGTGAATGTGGGAGAGGAGACATGCCAGGCGCTCTTCCAAGC
TTCAGGAGGGCTTGTCACGGAGCTTTGTTCGGTGTGCTGTCAGATCAGGATTCTCAGAGGGGATTGCAAGAGTTGTGGGAAAA
CTTATTTTGATAAATTATTACACATGCAGAAAACCTGATCACTGACTGGATCTGTCCACAACATGGAAAATAAACTGGATTTT
CAGTAAAAAAAAAAAAAAAAAAAAAAAAAAAAAAAA
```

Putative Amino Acid Domain Homology Analysis of mGPBP

Figure 3
(A)
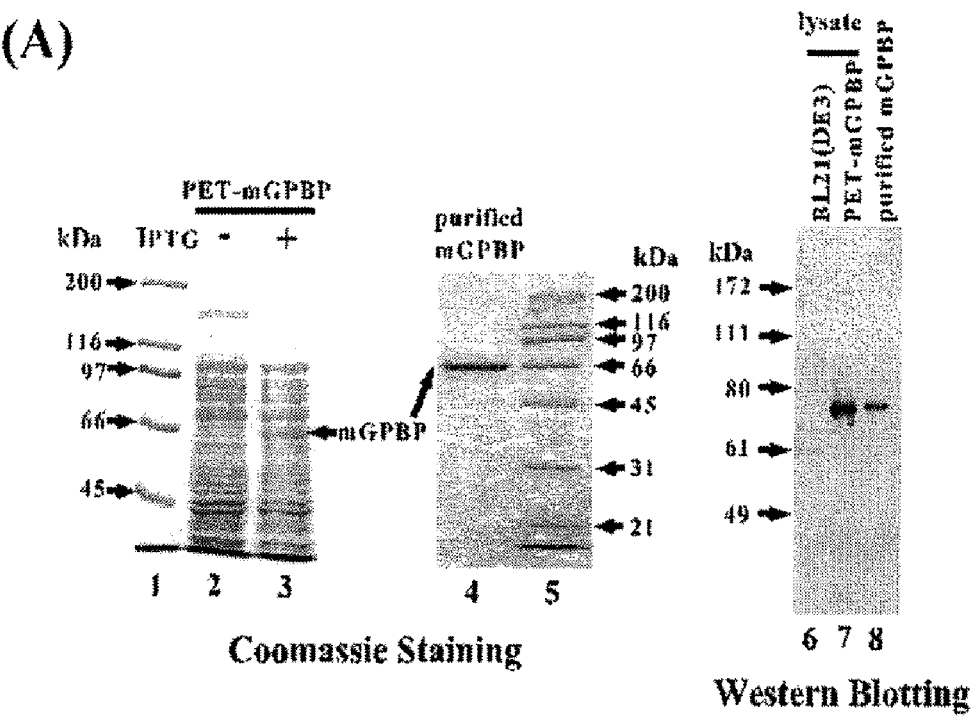
Coomassie Staining | Western Blotting
(B)
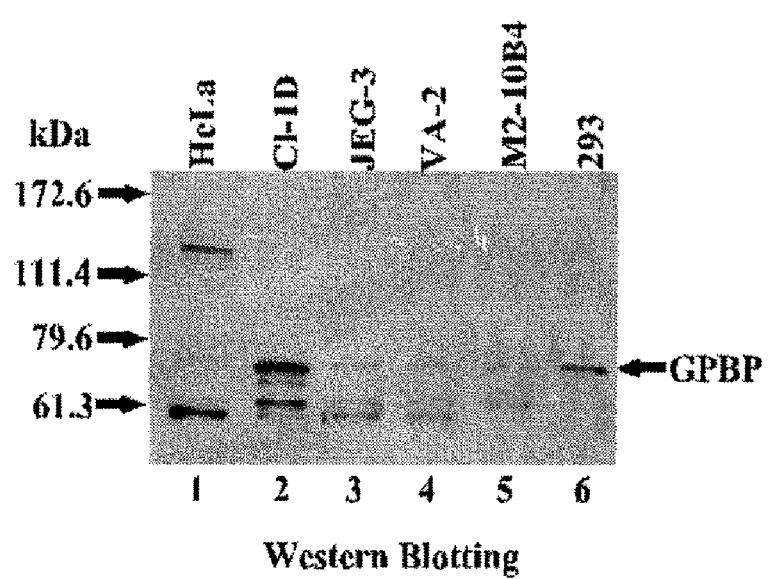
Western Blotting

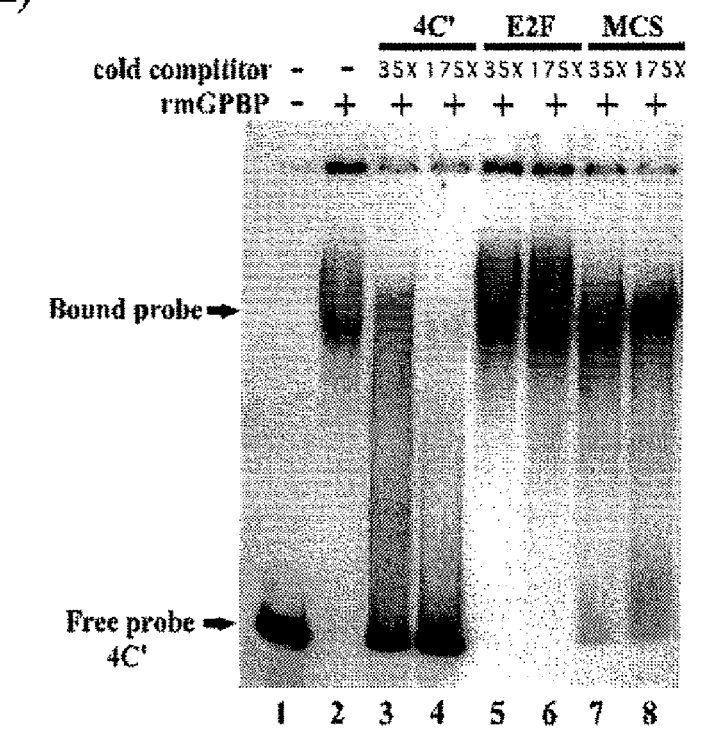
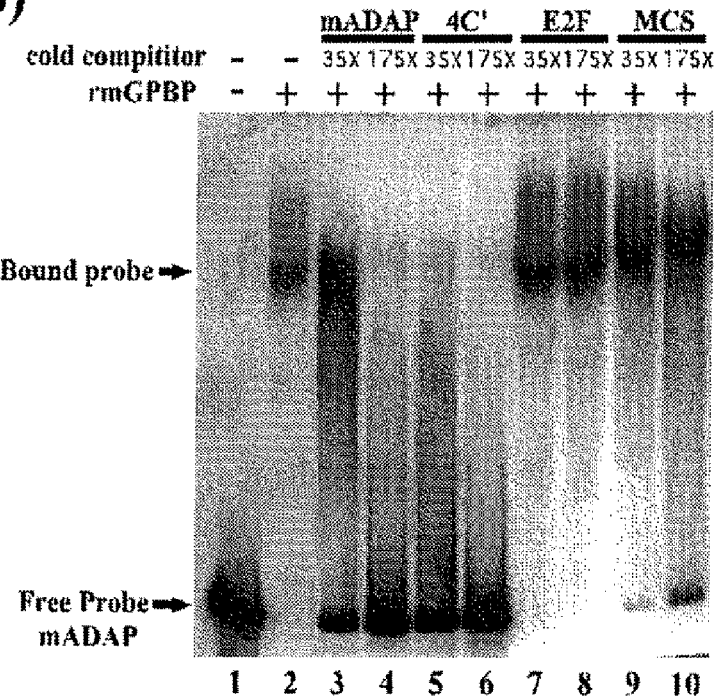
Figure 4

Figure 8A

5'-
ACTCACTATAGGGCTCGAGCGGCCGCCCGGGCAGGTCGGCGCCATTTTGGGACTGAGACTGGTTGTGGGGGA
GGGAAAAGCGGCAAAAGGGGATTATTCAAAGTACCGAAAACCTTCTCCCGGGATCAGGCGCGGCGGCACCCC
CAGGCCAGGGGCACCTCTGGTGGGGCAGAAGGTGATTGAATTACTCAGATATGAAGATCATCATCTAGGTTT
TGTGTAAAAGGCCCTGGATATTTTAAGTGGCCATTTTGGATTTACAGTGTTTTTGGATAATTTTGCCCCAGA
AGTTTATTAAAATTGGCAAGAATCGTCTGTGAAGTGAATTGATAGTAGTGAACAATTCAGCAAGCTACTTAA
AAAGAGACCCAGGCAGCATTTCTTCAGTATTTTGGTTCAAACGGATTATATAACTGGTTACAGTATTTCAGC
TGGTGGTAATTTTTGCCTCCCCTTCCCCCACCCCGTTGTTGGGGTTCTTCAGCCGAAACTGAGAGACGTTGA
TTTGTGTACTGAGTAGTTTCAGCAGTTTCAAATGACTGAGTATTGCTGAAGTTTCATGGCAGTTTATTTTTA
CCTTTATTGAAAGTTTTAGGAATTTTTGACTTCAGCTCTTTCATGTCACAATGGGACACTTTTTCTGAATGA
AGAGATTGAAAGAATACAGAGTTTTTTTCCTTTTATCTTTTATTTACGTGGAAATTTAAGATGTTGCAGTTT
TCCGGCAGCATGGTAGTATTGAGATAGCTATGTGTGTCTCTGTATATGCTGATGTTTAGGAATGCTCTTCAG
ATGTGAAATTTTCTTTTTGTTTTTGCTTTTTGGCTCGTAAATTGGATATTTCATCTGGAGTGGACAAGTACA
ACAGTGGCAAGTACATGGAATAATAAAGAAGACTTTGATCTTAAATCTAAAGAACTTGGCTAATTCGGGAGA
TAGCCATATGAAAACTTTAAAACAGAAGTATGGGTAGCTGACTTGAAGTAACTCTATGTCAAATAGTCGTAG
GTTAAGTATCTTCAAAGAACTTCGATATTATTTCAGAGGATACAAAATAAAAATACAAACTGGAAAATAAAG
ATTACAGAGAAAAAACCAACACCTTCCTGTGCAGTCCTGTTGGAATTTGGACTTGCCATGAGGTGTTGAAGC
CTTGTTTCACTGAGTTGGAGAGACTGGACCTAA<u>ATG</u> <u>GCG</u> <u>CAG</u> <u>CAT</u> <u>GAC</u> <u>TTT</u> <u>GCT</u> <u>CCA</u>
                                                            Met Ala Gln His Asp Phe Ala Pro
<u>GCC</u> <u>TGG</u> <u>CTT</u> <u>AAT</u> <u>TTC</u> <u>CCT</u> <u>ACT</u> <u>CCA</u> <u>CCA</u> <u>TCA</u> <u>TCA</u> <u>ACA</u> <u>AAG</u> <u>TCG</u> <u>TCA</u> <u>TTG</u>
Ala Trp Leu Asn Phe Pro Thr Pro Pro Ser Ser Thr Lys Ser Ser Leu
<u>AAT</u> <u>TTT</u> <u>GAG</u> <u>AAG</u> <u>CAT</u> <u>TCT</u> <u>GAA</u> <u>AAC</u> <u>TTT</u> <u>GCA</u> <u>TGG</u> <u>ACA</u> <u>GAG</u> <u>AAT</u> <u>CGT</u> <u>TAT</u>
Asn Phe Glu Lys His Ser Glu Asn Phe Ala Trp Thr Glu Asn Arg Tyr
<u>GAT</u> <u>GTG</u> <u>AAC</u> <u>CGT</u> <u>CGA</u> <u>CGA</u> <u>CAC</u> <u>AAC</u> <u>TCT</u> <u>TCA</u> <u>GAT</u> <u>GGC</u> <u>TTT</u> <u>GAT</u> <u>TCT</u> <u>GCT</u>
Asp Val Asn Arg Arg Arg His Asn Ser Ser Asp Gly Phe Asp Ser Ala
<u>ATT</u> <u>GGA</u> <u>CGT</u> <u>CCT</u> <u>AAT</u> <u>GGA</u> <u>GGT</u> <u>AAC</u> <u>TTT</u> <u>GGA</u> <u>AGG</u> <u>AAA</u> <u>GAA</u> <u>AAA</u> <u>AAT</u> <u>GGA</u>
Ile Gly Arg Pro Asn Gly Gly Asn Phe Gly Arg Lys Glu Lys Asn Gly
<u>TGG</u> <u>CGT</u> <u>ACA</u> <u>CAT</u> <u>GGA</u> <u>AGA</u> <u>AAT</u> <u>GGT</u> <u>ACA</u> <u>GAA</u> <u>AAC</u> <u>ATA</u> <u>AAT</u> <u>CAT</u> <u>CGA</u> <u>GGT</u>
Trp Arg Thr His Gly Arg Asn Gly Thr Glu Asn Ile Asn His Arg Gly
<u>GGA</u> <u>TAC</u> <u>CAT</u> <u>GGT</u> <u>GGA</u> <u>AGT</u> <u>TCC</u> <u>CGT</u> <u>TCT</u> <u>CGT</u> <u>AGC</u> <u>AGT</u> <u>ATT</u> <u>TTC</u> <u>CAT</u> <u>GCA</u>
Gly Tyr His Gly Gly Ser Ser Arg Ser Arg Ser Ser Ile Phe His Ala
<u>GGA</u> <u>AAA</u> <u>AGC</u> <u>CAA</u> <u>GGA</u> <u>CTA</u> <u>CAT</u> <u>GAA</u> <u>AAC</u> <u>AAC</u> <u>ATA</u> <u>CCT</u> <u>GAC</u> <u>AAT</u> <u>GAA</u> <u>ACC</u>
Gly Lys Ser Gln Gly Leu His Glu Asn Asn Ile Pro Asp Asn Glu Thr
<u>GGG</u> <u>AGG</u> <u>AAA</u> <u>GAA</u> <u>GAC</u> <u>AAG</u> <u>AGA</u> <u>GAA</u> <u>CGC</u> <u>AAA</u> <u>CAG</u> <u>TTT</u> <u>GAA</u> <u>GCT</u> <u>GAG</u> <u>GAT</u>
Gly Arg Lys Glu Asp Lys Arg Glu Arg Lys Gln Phe Glu Ala Glu Asp
<u>TTT</u> <u>CCG</u> <u>TCT</u> <u>TTA</u> <u>AAT</u> <u>CCT</u> <u>GAG</u> <u>TAT</u> <u>GAG</u> <u>AGA</u> <u>GAA</u> <u>CCA</u> <u>AAT</u> <u>CAC</u> <u>AAT</u> <u>AAG</u>
Phe Pro Ser Leu Asn Pro Glu Tyr Glu Arg Glu Pro Asn His Asn Lys
<u>TCT</u> <u>TTA</u> <u>GCT</u> <u>GCA</u> <u>GGT</u> <u>GTG</u> <u>TGG</u> <u>GGC</u> <u>CTA</u> <u>CAC</u> <u>GCC</u> <u>CAG</u> <u>ACA</u> <u>CAC</u> <u>ACA</u> <u>TAC</u>
Ser Leu Ala Ala Gly Val Trp Gly Leu His Ala Gln Thr His Thr Tyr
<u>CCA</u> <u>ACC</u> <u>AAA</u> <u>AAA</u> <u>ATC</u> <u>TCC</u> <u>CAA</u> <u>GCT</u> <u>CCT</u> <u>CTC</u> <u>TTA</u> <u>GAA</u> <u>TAT</u> <u>CCT</u> <u>CCG</u> <u>AAT</u>
Pro Thr Lys Lys Ile Ser Gln Ala Pro Leu Leu Glu Tyr Pro Pro Asn
<u>CCT</u> <u>AAA</u> <u>TCT</u> <u>AGA</u> <u>GCT</u> <u>CCA</u> <u>AGG</u> <u>ATG</u> <u>CTG</u> <u>GTC</u> <u>ATT</u> <u>AAG</u> <u>AAA</u> <u>GGT</u> <u>AAT</u> <u>ACA</u>
Pro Lys Ser Arg Ala Pro Arg Met Leu Val Ile Lys Lys Gly Asn Thr
<u>AAA</u> <u>GAC</u> <u>TTA</u> <u>CAG</u> <u>CTA</u> <u>TCT</u> <u>GGA</u> <u>TTC</u> <u>CCA</u> <u>GTA</u> <u>GTA</u> <u>GGA</u> <u>AAT</u> <u>CTT</u> <u>CCG</u> <u>TCA</u>
Lys Asp Leu Gln Leu Ser Gly Phe Pro Val Val Gly Asn Leu Pro Ser
<u>CAG</u> <u>CCA</u> <u>GTT</u> <u>AAG</u> <u>AAT</u> <u>GGA</u> <u>ACT</u> <u>GGT</u> <u>CCA</u> <u>AGT</u> <u>GTT</u> <u>TAT</u> <u>AAA</u> <u>GGT</u> <u>TTA</u> <u>GTC</u>
Gln Pro Val Lys Asn Gly Thr Gly Pro Ser Val Tyr Lys Gly Leu Val
<u>CCT</u> <u>AAA</u> <u>CCT</u> <u>GCT</u> <u>GCT</u> <u>CCA</u> <u>CCT</u> <u>ACA</u> <u>AAA</u> <u>CCT</u> <u>ACA</u> <u>CAA</u> <u>TGG</u> <u>AAA</u> <u>AGC</u> <u>CAA</u>
Pro Lys Pro Ala Ala Pro Pro Thr lys Pro Thr Gln Trp Lys Ser Gln
<u>ACA</u> <u>AAA</u> <u>GAA</u> <u>AAT</u> <u>AAA</u> <u>GTT</u> <u>GGA</u> <u>ACT</u> <u>TCT</u> <u>TTC</u> <u>CCT</u> <u>CAT</u> <u>GAG</u> <u>TCC</u> <u>ACA</u> <u>TTT</u>
Thr Lys Glu Asn Lys Val Gly Thr Ser Phe Pro His Glu Ser Thr Phe
<u>GGC</u> <u>GTT</u> <u>GGC</u> <u>AAC</u> <u>TTT</u> <u>AAT</u> <u>GCT</u> <u>TTT</u> <u>AAA</u> <u>TCA</u> <u>ACT</u> <u>GCC</u> <u>AAG</u> <u>AAC</u> <u>TTT</u> <u>AGT</u>
Gly Val Gly Asn Phe Asn Ala Phe Lys Ser Thr Ala Lys Asn Phe Ser
<u>CCA</u> <u>TCT</u> <u>ACA</u> <u>AAT</u> <u>TCA</u> <u>GTG</u> <u>AAA</u> <u>GAG</u> <u>TGT</u> <u>AAT</u> <u>CGC</u> <u>TCA</u> <u>AAT</u> <u>TCC</u> <u>TCT</u> <u>TCT</u>
Pro Ser Thr Asn Ser Val Lys Glu Cys Asn Arg Ser Asn Ser Ser Ser
<u>CCT</u> <u>GTT</u> <u>GAC</u> <u>AAA</u> <u>CTT</u> <u>AAT</u> <u>CAG</u> <u>CAG</u> <u>CCT</u> <u>CGT</u> <u>CTA</u> <u>ACC</u> <u>AAA</u> <u>CTG</u> <u>ACA</u> <u>CGA</u>
Pro Val Asp Lys Leu Asn Gln Gln Pro Arg Leu Thr Lys Leu Thr Arg

Figure 8B

```
ATG CGC ACT GAT AAG AAG AGT GAA TTT TTG AAA GCA TTG AAA AGA GAC
Met Arg Thr Asp Lys Lys Ser Glu Phe Leu Lys Ala Leu Lys Arg Asp
AGA GTA GAA GAG GAA CAT GAA GAT GAA AGC CGT GCT GGC TCA GAG AAG
Arg Val Glu Glu Glu His Glu Asp Glu Ser Arg Ala Gly Ser Glu Lys
GAT GAC GAC TCA TTT AAT TTA CAT AAC AGC AAT AGT ACT CAC CAA GAA
Asp Asp Asp Ser Phe Asn Leu His Asn Ser Asn Ser Thr His Gln Glu
AGG GAT ATA AAC CGA AAC TTC GAT GAA AAT GAA ATT CCT CAA GAG AAT
Arg Asp Ile Asn Arg Asn Phe Asp Glu Asn Glu Ile Pro Gln Glu Asn
GGC AAT GCC TCA GTG ATT TCC CAG CAG ATC ATT CGG TCT TCA ACC TTC
Gly Asn Ala Ser Val Ile Ser Gln Gln Ile Ile Arg Ser Ser Thr Phe
CCA CAA ACT GAT GTT CTT TCA AGT TCA CTT GAG GCA GAA CAC AGA TTG
Pro Gln Thr Asp Val Leu Ser Ser Ser Leu Glu Ala Glu His Arg Leu
TTA AAG GAA ATG GGC TGG CAG GAA GAC AGT GAA AAT GAT GAA ACA TGT
Leu Lys Glu Met Gly Trp Gln Glu Asp Ser Glu Asn Asp Glu Thr Cys
GCT CCC TTA ACT GAG GAT GAA ATG AGA GAA TTC CAA GTT ATT AGT GAA
Ala Pro Leu Thr Glu Asp Glu Met Arg Glu Phe Gln Val Ile Ser Glu
CAG TTA CAG AAG AAT GGT CTG AGA AAA AAT GGT ATT TTG AAA AAT GGC
Gln Leu Gln Lys Asn Gly Leu Arg Lys Asn Gly Ile Leu Lys Asn Gly
TTG ATC TGT GAC TTC AAG TTT GGA CCG TGG AAG AAC AGC ACT TTC AAA
Leu Ile Cys Asp Phe Lys Phe Gly Pro Trp Lys Asn Ser Thr Phe Lys
CCC ACA ACT GAG AAT GAT GAC ACA GAG ACA AGT AGC AGT GAT ACA TCA
Pro Thr Thr Glu Asn Asp Asp Thr Glu Thr Ser Ser Ser Asp Thr Ser
GAT GAC GAC GAT GTG TGAAGGATTTCCTAACAGCTTTAGAAATCTTAGTGTGATACAT
Asp Asp Asp Asp Val
CTCTCATACAGTTTGGGGTGAATTGTAAAAATGAAGAACTATAATTTATGTAGTGAAATACCCCATTAGAAG
AGGATTTTTTGGGGGACTTCAATATGAAGAAAACCAAGAATGTTTTGTTGGGCTGTGTTAACATTATTTCT
TTGTAAATGAATGTTGTAGGGATTGAGGACTTGGGTTGGTCCAACATTGACTTTCTTCATCACTGCAACATT
TCTCTGACTAGCAATGTGACGATGTAACAAATGAGATTTTCTCATTTAATAATAAAAAATTGTGTAATGTTT
TGCAAAGCTTCTGTCTTAAAATGTCCAGGTCTTAAGAAAAAAGGCAGCTTACACTGTTTTGCTTGCAGAGTC
ATATCTTTTTCGTACAATGGAAATCCTCAAGTCCACTTTGTGCGGTCTCCCTCTCCTTCCCCAAAAAACAA
CAACAACAAAACAAAAACCAAAAAGGAAATGTAGCATGTTGGCTAAAACTGGAGCAAAGTGCACTAAAACA
ATTTCCTGAACTCACCTGTTGTACTATTCACCTTTTAAACCATAAATTGCTCTTTAGCCATTTGTAGTGCAG
TAAATGTTACAGGAAAAGACTTGGCACATTTTCTTCCAAATTTCAAGAGGTGATTTTCAAAAGCTTTATTGG
GGTATGTTGTCAGACCAGGGTTTTCAGAGTTGATGGAAAAGAGTCTTGTGAGAAACTTATTTTGATAAATT
ATTACACACGCAGAAAAACTGATCACACTGACTGGATCTGTCCACGACATGGAAAATAAACTGGATTTTCAG
AATATTGTTG-3'
```

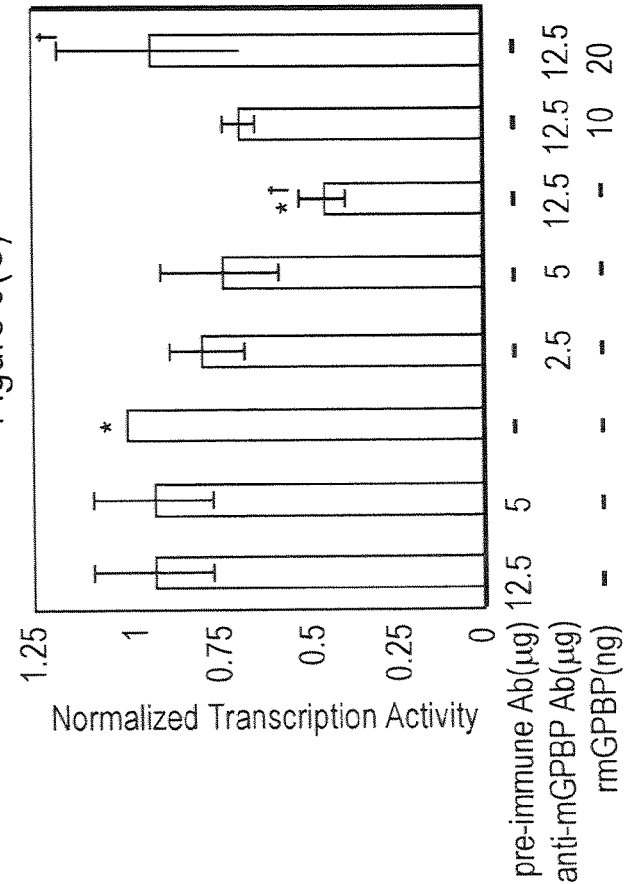
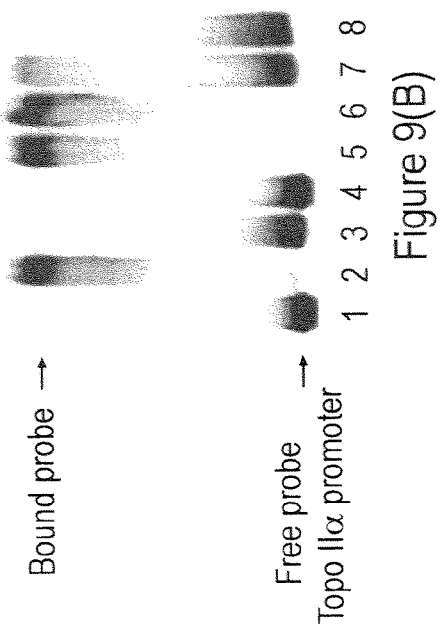
Figure 9(A)
Figure 9(B)
Figure 9(C)

SEQUENCE LISTING

```
<160> NUMBER OF SEQ ID NOS: 13

<210> SEQ ID NO 1
<211> LENGTH: 3482
<212> TYPE: DNA
<213> ORGANISM: Mus musculus
```

-continued

```
<400> SEQUENCE: 1
ctagaattca gcggccgctg aattctagaa tgagactggt tgtggggag ggaaaagcgg        60 caaaagggga ttattcaaag taccgaaaac ctcctcccgg gatcgagcgc agcggcaccc      120
ccaggccagg ggcacctctg gtggggcaga aggtggttga atttggcgta tgaagatcat      180
catctaggtt ttgtttaaaa ggccccggat atttcaagtg gccattttgg aattacagtt      240 ttgttttttgt tttgggcaat tttgctccag aagttcatta aaattgacaa gaatcatctc      300
tgaagtgaat tgatagtagt gaacaaattc aacgagctac taaaagtccc agccatttct      360
tcagtatttt gggtcaaacg gattatataa gtggttaaag catttcatct ggtgttattt      420
ttgtctcttt cccctctcct gtttgtgttc ttcagccaaa actgtaagat atgtttgatt      480
tgtgtaccaa gtagtttcag cagtttcaaa ttactgttta aatattgctg aagttttgtg      540
gcagttcttt ttaccttttat taaaagtttt agtaattttt gacttcagct tttttcatat      600
tacaatggga cagcttttct aaatgaagac attgaaagaa tacagcgttt ttttcttttt      660
atcttttatt tacttgggaa tgtaagatgt tccattttca caccagcatg gtagtattga      720
gatagctatt tgtctataca cgctgatgtt tagaagtaat cttcagatgt gaaattttc      780 tttttgtttc tgcttttgg cacataaatt ggctatttct tctggagtgg ataagtacaa      840
cagtgacaaa tacatggaac agtaaagaag accttgctct taaatccaag gaacctggct      900
aactctggat ctgaccatat gaaaacttca agtaaatat gggtagctga cttcaagtaa      960
ctctatgtca aatagtcata ggttaagtat cttcaaagaa cttggatatt tcagaggata     1020
caaaataaaa aaacaaactg gaaaacataa agcttataga gaagaaatca acaccttctt     1080
gtgcagtcct tttggaattt ggacttgcca tgaggtgttg aagccttgtt tcactgagtt     1140
ggagagactg gacctaaatg gcgcagcatg actttgctcc agcctggctt aattttccta     1200
ctcctccatc atcaacaaag tcatcattga attttgagaa gcactctgaa aatttttcat     1260
ggacagaaaa tcgttatgat gtgagtcgtc gacgacacaa ttcttcagat ggctttgatt     1320
ctggtattgg acgtcctaat ggaggtaatt ttgggaggaa agagaaaaat ggatggcgta     1380
cgcatggcag aaatggtaca gaaaacataa atcatcgtgg gggataccat ggtggaaatt     1440
cccgttctcg tagcagtatt ttccattctg gaaaaagcca aggactacat gaaaacagca     1500
tccctgacaa tgaaactggg aggaaagaag acaaaagaga acgcagacag tttgaggctg     1560
aggattttcc atctttaaat cctgaatatg agagagaacc aaatcagaat aaatctttag     1620
ctgcgggtgt ttggggccta cacgcccaga cacacacata cccaaccaaa aaaatctccc     1680
aagctcctct cttagactat cccccgaatc ctaaatctag aactccaaga atgctggtca     1740
ttaagaaagg taatacaaaa gacttacagc tatctggatt cccagtagca ggaaacctcc     1800
agtcacagcc agttaagaat ggaactagtc caagtgttta taaggctta gtccccaaac     1860 ctgctgttcc acctacaaaa cctacacaat ggaaaagcca aactaaagaa aacaaagtcg     1920
ggacttcttt ttctcatgaa tctacatatg gtgttggcaa ctttaatact tttaagtcaa     1980
cggccaagaa tattagtcca tcaacaaatt cagtgaaaga gtgtaatcgt tcaaattctt     2040
cttcgcctgt tgacaaactt aatcagcagc ctcgtttaac taaactgaca cgaatgcgca     2100
gcgataaaaa gagtgaattt ttgaaagcat tgaaaggga cagagtggag gaggaacatg     2160
aagatgaaag tcatgctggc tcagagaagg acgacgactc atttaatttg cataacagca     2220
atactactca ccaagaaaga gatataaaca gaaactttga tgaaaatgaa attccacagg     2280
agaacggcaa tgcctcgata atttctcaac agatcattcg ttcttcaact tttccacaaa     2340
```

-continued

```
ctgatgttct ttccagttca ctagaggcag aacacagatt attaaaagaa atgggctggc    2400
aggaagacag tgaaaatgat gaaacatgtg ctcccttaac tgaggatgaa atgagagaat    2460
tccaagttat tagtgaacag ttacagaaga atggtctgag aaaaaatggt attttgaaaa    2520
atggcctgat ctgtgacttc aagtttggac cctggaaaaa cagcactttc aaacccacaa    2580
ttgagaatga tgacacagag acaagtagca gcgacacgtc ggatgatgac gatgtgtgaa    2640
ggagatcctc acagctttag aaatgttagt gtgatacatc tctcatgcag tttggggtga    2700
ttgtaaaaat gaagaactat aatttatgta gtgaacctac cccattagaa gatgattttt    2760
tgggggactt cgatatgaag aaaaccaaga atgttgtgtt gggctgtgtt gaacattatt    2820
tctttgtaaa tgaatgttgt agaaatgagg actttggttg atccaacatt gactttcttc    2880
atcactgcag catttctctt gactagcaat gtgacgatgt aacaaatgag attttctcat    2940
ttaataataa aaaattgtgt gatgttttgc aaagcttctg tcttaaaatg ttcaggtctt    3000
aaggtacaag gcagcttaca gttttgcttg cagagtccta tcttttttcaa actgtggaaa    3060 tcttcaactc tacgtgtgca cctccttatc cactccccct aaaacaaaac aacagcaaaa    3120
aggaaaatgt agcatgttgg ctaaaaccgg agcagagtga ctaaaacatt agcttcttga    3180
actcaactct tgtactaagt cacctttcca aacaaattcc tctttagtct ttggtagcag    3240
tgaatgtggg agaggagaca tgccaggcgc tcttccaagc ttcaggaggg gcttgtcagg    3300
agctttgttc ggtgtgctgt cagatcagga ttctcagagg ggattgcaag agttgtggga    3360 aaacttatt tgataaatta ttacacatgc agaaaacctg atcactgact ggatctgtcc    3420
acaacatgga aaataaactg gattttcagt aaaaaaaaaa aaaaaaaaaa aaaaaaaaaa    3480
aa                                                                  3482
```

<210> SEQ ID NO 2
<211> LENGTH: 493
<212> TYPE: PRT
<213> ORGANISM: Mus musculus

<400> SEQUENCE: 2

```
Met Ala Gln His Asp Phe Ala Pro Ala Trp Leu Asn Phe Pro Thr Pro
1               5                   10                  15

Pro Ser Ser Thr Lys Ser Ser Leu Asn Phe Glu Lys His Ser Glu Asn
                20                  25                  30

Phe Ser Trp Thr Glu Asn Arg Tyr Asp Val Ser Arg Arg His Asn
            35                  40                  45

Ser Ser Asp Gly Phe Asp Ser Gly Ile Gly Arg Pro Asn Gly Gly Asn
        50                  55                  60

Phe Gly Arg Lys Glu Lys Asn Gly Trp Arg Thr His Gly Arg Asn Gly
65                  70                  75                  80

Thr Glu Asn Ile Asn His Arg Gly Gly Tyr His Gly Gly Asn Ser Arg
                85                  90                  95

Ser Arg Ser Ser Ile Phe His Ser Gly Lys Ser Gln Gly Leu His Glu
            100                 105                 110

Asn Ser Ile Pro Asp Asn Glu Thr Gly Arg Lys Glu Asp Lys Arg Glu
        115                 120                 125

Arg Arg Gln Phe Glu Ala Glu Asp Phe Pro Ser Leu Asn Pro Glu Tyr
    130                 135                 140

Glu Arg Glu Pro Asn Gln Asn Lys Ser Leu Ala Ala Gly Val Trp Gly
145                 150                 155                 160
```

```
Leu His Ala Gln Thr His Thr Tyr Pro Thr Lys Lys Ile Ser Gln Ala
            165                 170                 175

Pro Leu Leu Asp Tyr Pro Pro Asn Pro Lys Ser Arg Thr Pro Arg Met
        180                 185                 190

Leu Val Ile Lys Lys Gly Asn Thr Lys Asp Leu Gln Leu Ser Gly Phe
    195                 200                 205

Pro Val Ala Gly Asn Leu Gln Ser Gln Pro Val Lys Asn Gly Thr Ser
210                 215                 220

Pro Ser Val Tyr Lys Gly Leu Val Pro Lys Pro Ala Val Pro Pro Thr
225                 230                 235                 240

Lys Pro Thr Gln Trp Lys Ser Gln Thr Lys Glu Asn Lys Val Gly Thr
                245                 250                 255

Ser Phe Ser His Glu Ser Thr Tyr Gly Val Gly Asn Phe Asn Thr Phe
            260                 265                 270

Lys Ser Thr Ala Lys Asn Ile Ser Pro Ser Thr Asn Ser Val Lys Glu
        275                 280                 285

Cys Asn Arg Ser Asn Ser Ser Pro Val Asp Lys Leu Asn Gln Gln
    290                 295                 300

Pro Arg Leu Thr Lys Leu Thr Arg Met Arg Ser Asp Lys Lys Ser Glu
305                 310                 315                 320

Phe Leu Lys Ala Leu Lys Arg Asp Arg Val Glu Glu Glu His Glu Asp
                325                 330                 335

Glu Ser His Ala Gly Ser Glu Lys Asp Asp Asp Ser Phe Asn Leu His
            340                 345                 350

Asn Ser Asn Thr Thr His Gln Glu Arg Asp Ile Asn Arg Asn Phe Asp
        355                 360                 365

Glu Asn Glu Ile Pro Gln Glu Asn Gly Asn Ala Ser Ile Ile Ser Gln
    370                 375                 380

Gln Ile Ile Arg Ser Ser Thr Phe Pro Gln Thr Asp Val Leu Ser Ser
385                 390                 395                 400

Ser Leu Glu Ala Glu His Arg Leu Leu Lys Glu Met Gly Trp Gln Glu
                405                 410                 415

Asp Ser Glu Asn Asp Glu Thr Cys Ala Pro Leu Thr Glu Asp Glu Met
            420                 425                 430

Arg Glu Phe Gln Val Ile Ser Glu Gln Leu Gln Lys Asn Gly Leu Arg
        435                 440                 445

Lys Asn Gly Ile Leu Lys Asn Gly Leu Ile Cys Asp Phe Lys Phe Gly
    450                 455                 460

Pro Trp Lys Asn Ser Thr Phe Lys Pro Thr Ile Glu Asn Asp Asp Thr
465                 470                 475                 480

Glu Thr Ser Ser Ser Asp Thr Ser Asp Asp Asp Val
                485                 490

<210> SEQ ID NO 3
<211> LENGTH: 3509
<212> TYPE: DNA
<213> ORGANISM: Homo sapiens

<400> SEQUENCE: 3
actcactata gggctcgagc ggccgcccgg gcaggtcggc gccatttggg gactgagact      60
ggttgtgggg gagggaaaag cggcaaaagg ggattattca agtaccgaa  aaccttctcc    120 cgggatcagg cgcggcggca ccccaggcc  agggcaccct ctggtggggc agaaggtgat    180
tgaattactc agatatgaag atcatcatct aggttttgtg taaaaggccc  tggatatttt    240
```

| | |
|---|---|
| aagtggccat tttggattta cagtgttttt ggataatttt gccccagaag tttattaaaa | 300 |
| ttggcaagaa tcgtctgtga agtgaattga tagtagtgaa caattcagca agctacttaa | 360 |
| aaagagaccc aggcagcatt tcttcagtat tttggttcaa acggattata taactggtta | 420 |
| cagtatttca gctggtggta atttttgcct cccttcccc accccgttg ttggggttct | 480 |
| tcagccgaaa ctgagagacg ttgatttgtg tactgagtag tttcagcagt ttcaaatgac | 540 |
| tgagtattgc tgaagtttca tggcagttta ttttaccttt tattgaaagt tttaggaatt | 600 |
| tttgacttca gctctttcat gtcacaatgg gacactttt ctgaatgaag agattgaaag | 660 |
| aatacagagt ttttttcctt ttatcttta tttacgtgga aatttaagat gttgcagttt | 720 |
| tccggcagca tggtagtatt gagatagcta tgtgtgtctc tgtatatgct gatgtttagg | 780 |
| aatgctcttc agatgtgaaa ttttcttttt gttttgctt tttggctcgt aaattggata | 840 |
| tttcatctgg agtggacaag tacaacagtg gcaagtacat ggaataataa agaagacttt | 900 |
| gatcttaaat ctaaagaact tggctaattc gggagatagc catatgaaaa ctttaaaaca | 960 |
| gaagtatggg tagctgactt gaagtaactc tatgtcaaat agtcgtaggt taagtatctt | 1020 |
| caaagaactt cgatattatt tcagaggata caaaataaaa atacaaactg gaaaataaag | 1080 |
| attacagaga aaaaccaac accttcctgt gcagtcctgt tggaatttgg acttgccatg | 1140 |
| aggtgttgaa gccttgtttc actgagttgg agagactgga cctaaatggc gcagcatgac | 1200 |
| tttgctccag cctggcttaa tttccctact ccaccatcat caacaaagtc gtcattgaat | 1260 |
| tttgagaagc attctgaaaa cttttgcatgg acagagaatc gttatgatgt gaaccgtcga | 1320 |
| cgacacaact cttcagatgg ctttgattct gctattggac gtcctaatgg aggtaacttt | 1380 |
| ggaaggaaag aaaaaaatgg atggcgtaca catggaagaa atggtacaga aaacataaat | 1440 |
| catcgaggtg gataccatgg tggaagttcc cgttctcgta gcagtatttt ccatgcagga | 1500 |
| aaaagccaag gactacatga aaacaacata cctgacaatg aaaccgggag gaaagaagac | 1560 |
| aagagagaac gcaaacagtt tgaagctgag gattttccgt ctttaaatcc tgagtatgag | 1620 |
| agagaaccaa atcacaataa gtctttagct gcaggtgtgt ggggcctaca cgcccagaca | 1680 |
| cacacatacc caaccaaaaa aatctcccaa gctcctctct tagaatatcc tccgaatcct | 1740 |
| aaatctagag ctccaaggat gctggtcatt aagaaaggta atacaaaaga cttacagcta | 1800 |
| tctggattcc cagtagtagg aaatcttccg tcacagccag ttaagaatgg aactggtcca | 1860 |
| agtgttata aaggtttagt ccctaaacct gctgctccac ctacaaaacc tacacaatgg | 1920 |
| aaaagccaaa caaagaaaa taagttgga acttctttcc ctcatgagtc cacatttggc | 1980 |
| gttggcaact ttaatgcttt taaatcaact gccaagaact ttagtccatc tacaaattca | 2040 |
| gtgaaagagt gtaatcgctc aaattcctct tctcctgttg acaaacttaa tcagcagcct | 2100 |
| cgtctaacca aactgacacg aatgcgcact gataagaaga gtgaatttt gaaagcattg | 2160 |
| aaaagagaca gagtagaaga ggaacatgaa gatgaaagcc gtgctggctc agagaaggat | 2220 |
| gacgactcat ttaatttaca taacagcaat agtactcacc aagaaaggga tataaaccga | 2280 |
| aacttcgatg aaaatgaaat tcctcaagag aatggcaatg cctcagtgat tcccagcag | 2340 |
| atcattcggt cttcaaccct cccacaaact gatgttcttt caagttcact tgaggcagaa | 2400 |
| cacagattgt taaggaaat gggctggcag gaagacagtg aaaatgatga acatgtgct | 2460 |
| cccttaactg aggatgaaat gagagaattc caagttatta gtgaacagtt acagaagaat | 2520 |
| ggtctgagaa aaaatggtat tttgaaaaat ggcttgatct gtgacttcaa gtttggaccg | 2580 |
| tggaagaaca gcactttcaa acccacaact gagaatgatg acacagagac aagtagcagt | 2640 |

-continued

```
gatacatcag atgacgacga tgtgtgaagg atttcctaac agctttagaa atcttagtgt   2700
gatacatctc tcatacagtt tggggtgaat tgtaaaaatg aagaactata atttatgtag   2760
tgaaataccc cattagaaga ggattttttg ggggacttca atatgaagaa accaagaat    2820
gttttgttgg gctgtgttga acattattc tttgtaaatg aatgttgtag ggattgagga    2880
cttgggttgg tccaacattg actttcttca tcactgcaac atttctctga ctagcaatgt   2940
gacgatgtaa caaatgagat tttctcattt aataataaaa aattgtgtaa tgttttgcaa   3000
agcttctgtc ttaaaatgtc caggtcttaa gaaaaaaggc agcttacact gttttgcttg   3060
cagagtcata tcttttcgt acaatggaaa tcctcaagtc cactttgtgc ggtctccctc    3120
tccttccccc aaaaaacaac aacaacaaaa caaaaaccaa aaaggaaaat gtagcatgtt   3180
ggctaaaact ggagcaaagt gcactaaaac aatttcctga actcacctgt tgtactattc   3240
accttttaaa ccataaattg ctctttagcc atttgtagtg cagtaaatgt tacaggaaaa   3300
gacttggcac attttcttcc aaatttcaag aggtgatttt caaaagcttt attggggtat   3360
gttgtcagac cagggttttc agagttgatg gaaaagagtc ttgtgagaaa acttattttg   3420
ataaattatt acacacgcag aaaaactgat cacactgact ggatctgtcc acgacatgga   3480
aaataaactg gattttcaga atattgttg                                     3509

<210> SEQ ID NO 4
<211> LENGTH: 495
<212> TYPE: PRT
<213> ORGANISM: Homo sapiens

<400> SEQUENCE: 4

Met Ala Gln His Asp Phe Ala Pro Ala Trp Leu Asn Phe Pro Thr Pro
1               5                   10                  15

Pro Ser Ser Thr Lys Ser Ser Leu Asn Phe Glu Lys His Ser Glu Asn
                20                  25                  30

Phe Ala Trp Thr Glu Asn Arg Tyr Asp Val Asn Arg Arg His Asn
            35                  40                  45

Ser Ser Asp Gly Phe Asp Ser Ala Ile Gly Arg Pro Asn Gly Gly Asn
        50                  55                  60

Phe Gly Arg Lys Glu Lys Asn Gly Trp Arg Thr His Gly Arg Asn Gly
65                  70                  75                  80

Thr Glu Asn Ile Asn His Arg Gly Gly Tyr His Gly Gly Ser Ser Arg
                85                  90                  95

Ser Arg Ser Ile Phe His Ala Gly Lys Ser Gln Gly Leu His Glu
            100                 105                 110

Asn Asn Ile Pro Asp Asn Glu Thr Gly Arg Lys Glu Asp Lys Arg Glu
        115                 120                 125

Arg Lys Gln Phe Glu Ala Glu Asp Phe Pro Ser Leu Asn Pro Glu Tyr
    130                 135                 140

Glu Arg Glu Pro Asn His Asn Lys Ser Leu Ala Ala Gly Val Trp Gly
145                 150                 155                 160

Leu His Ala Gln Thr His Thr Tyr Pro Thr Lys Lys Ile Ser Gln Ala
                165                 170                 175

Pro Leu Leu Glu Tyr Pro Pro Asn Pro Lys Ser Arg Ala Pro Arg Met
            180                 185                 190

Leu Val Ile Lys Lys Gly Asn Thr Lys Asp Leu Gln Leu Ser Gly Phe
        195                 200                 205

Pro Val Val Gly Asn Leu Pro Ser Gln Pro Val Lys Asn Gly Thr Gly
    210                 215                 220
```

```
Pro Ser Val Tyr Lys Gly Leu Val Pro Lys Pro Ala Ala Pro Pro Thr
225                 230                 235                 240

Leu Tyr Ser Pro Thr Gln Trp Lys Ser Gln Thr Lys Glu Asn Lys Val
            245                 250                 255

Gly Thr Ser Phe Pro His Glu Ser Thr Phe Gly Val Gly Asn Phe Asn
        260                 265                 270

Ala Phe Lys Ser Thr Ala Lys Asn Phe Ser Pro Ser Thr Asn Ser Val
    275                 280                 285

Lys Glu Cys Asn Arg Ser Asn Ser Ser Pro Val Asp Lys Leu Asn
290                 295                 300

Gln Gln Pro Arg Leu Thr Lys Leu Thr Arg Met Arg Thr Asp Lys Lys
305                 310                 315                 320

Ser Glu Phe Leu Lys Ala Leu Lys Arg Asp Arg Val Glu Glu Glu His
            325                 330                 335

Glu Asp Glu Ser Arg Ala Gly Ser Glu Lys Asp Asp Asp Ser Phe Asn
        340                 345                 350

Leu His Asn Ser Asn Ser Thr His Gln Glu Arg Asp Ile Asn Arg Asn
    355                 360                 365

Phe Asp Glu Asn Glu Ile Pro Gln Glu Asn Gly Asn Ala Ser Val Ile
370                 375                 380

Ser Gln Gln Ile Ile Arg Ser Ser Thr Phe Pro Gln Thr Asp Val Leu
385                 390                 395                 400

Ser Ser Ser Leu Glu Ala Glu His Arg Leu Leu Lys Glu Met Gly Trp
            405                 410                 415

Gln Glu Asp Ser Glu Asn Asp Glu Thr Cys Ala Pro Leu Thr Glu Asp
        420                 425                 430

Glu Met Arg Glu Phe Gln Val Ile Ser Glu Gln Leu Gln Lys Asn Gly
    435                 440                 445

Leu Arg Lys Asn Gly Ile Leu Lys Asn Gly Leu Ile Cys Asp Phe Lys
    450                 455                 460

Phe Gly Pro Trp Lys Asn Ser Thr Phe Lys Pro Thr Thr Glu Asn Asp
465                 470                 475                 480

Asp Thr Glu Thr Ser Ser Ser Asp Thr Ser Asp Asp Asp Val
            485                 490                 495

<210> SEQ ID NO 5
<211> LENGTH: 2858
<212> TYPE: DNA
<213> ORGANISM: Homo sapiens

<400> SEQUENCE: 5
cggcaaaagg ggattattca aagtaccgaa aaccttctcc cgggatcagg cgcggcggca        60 ccccaggcc aggggcacct ctggtggggc agaaggtgat tgaattactc agatatgaag       120
atcatcatct aggttttgtg taaaaggccc tggatatttt aagtggccat tttgatttta       180
cagtgttttt ggataatttt gccccagaag tttattaaaa ttggcaagaa tcgtctgtga       240
agtgaattga tagtagtgaa caattcagca agctacttaa aaagagaccc aggcagcatt       300
tcttcagtat tttggttcaa acggattata taactggtta cagtatttca gctggtggta       360
atttttgcct cccttcccc cacccgttg ttgggttct tcagccgaaa ctgagagacg       420
ttgatttgtg tactgagtag tttcagcagt ttcaaatgac tgagtattgc tgaagtttca       480
tggcagttta tttttacctt tattgaaagt tttaggaatt tttgacttca gctctttcat       540
```

```
gtcacaatgg gacactttt  ctgaatgaag agattgaaag aatacagagt ttttttcctt   600
ttatctttta tttacgtgga aatttaagat gttgcagttt tccggcagca tggtagtatt   660
gagatagcta tgtgtgtctc tgtatatgct gatgtttagg aatgctcttc agatgtgaaa   720
ttttctttt  gttttgctt  tttggctcgt aaattggata tttcatctgg agtggacaag   780
tacaacagtg gcaagtacat ggaataataa agaagacttt gatcttaaat ctaaagaact   840
tggctaattc gggagatagc catatgaaaa ctttaaaaca gaagtatggg tagctgactt   900
gaagtaactc tatgtcaaat agtcgtaggt taagtatctt caaagaactt cgatattatt   960
tcagaggata caaataaaa  atacaaactg aaaataaag  attacagaga aaaaccaac   1020
accttcctgt gcagtcctgt tggaatttgg acttgccatg aggtgttgaa gccttgtttc  1080
actgagttgg agagactgga cctaaatggc gcagcatgac tttgctccag cctggcttaa  1140
tttccctact ccaccatcat caacaaagtc gtcattgaat tttgagaagc attctgaaaa  1200
ctttgcatgg acagagaatc gttatgatgt gaaccgtcga cgacacaact cttcagatgg  1260
ctttgattct gctattggac gtcctaatgg aggtaacttt ggaaggaaag aaaaaaatgg  1320
atggcgtaca catggaagaa atggtacaga aaacataaat catcgaggtg ataccatgg   1380
tggaagttcc cgttctcgta gcagtatttt ccatgcagga aaaagccaag gactacatga  1440
aaacaacata cctgacaatg aaaccgggag gaaagaagac aagagagaac gcaaacagtt  1500
tgaagctgag gattttccgt ctttaaatcc tgagtatgag agagaaccaa atcacaataa  1560
gtctttagct gcaggtgtgt gggaatatcc tccgaatcct aaatctagag ctccaaggat  1620
gctggtcatt aagaaaggta atacaaaaga cttacagcta tctggattcc cagtagtagg  1680
aaatcttccg tcacagccag ttaagaatgg aactggtcca agtgtttata aggtttagt   1740
ccctaaacct gctgctccac ctacaaaacc tacacaatgg aaaagccaaa caaagaaaa   1800
taaagttgga acttctttcc ctcatgagtc cacatttggc gttggcaact ttaatgcttt  1860
taaatcaact gccaagaact ttagtccatc tacaaattca gtgaaagagt gtaatcgctc  1920
aaattcctct tctcctgttg acaaacttaa tcagcagcct cgtctaacca aactgacacg  1980
aatgcgcact gataagaaga gtgaattttt gaaagcattg aaaagagaca gagtagaaga  2040
ggaacatgaa gatgaaagcc gtgctggctc agagaaggat gacgactcat ttaatttaca  2100
taacagcaat agtactcacc aagaaaggga tataaaccga aacttcgatg aaaatgaaat  2160
tcctcaagag aatggcaatg cctcagtgat ttcccagcag atcattcggt cttcaacctt  2220
cccacaaact gatgttcttt caagttcact tgaggcagaa cacagattgt taaaggaaat  2280
gggctggcag gaagacagtg aaaatgatga aacatgtgct cccttaactg aggatgaaat  2340
gagagaattc caagttatta gtgaacagtt acagaagaat ggtctgagaa aaaatggtat  2400
tttgaaaaat ggcttgatct gtgacttcaa gtttggaccg tggaagaaca gcactttcaa  2460
acccacaact gagaatgatg acacagagac aagtagcagt gatacatcag atgacgacga  2520
tgtgtgaagg atttcctaac agctttagaa atcttagtgt gatacatctc tcatacagtt  2580
tggggtgaat tgtaaaaatg aagaactata atttatgtag tgaaataccc cattagaaga  2640
ggatttttg  ggggacttca atatgaagaa aaccaagaat gttttgttgg gctgtgttga  2700
acattatttc tttgtaaatg aatgttgtag gaatgaggac ttgggttggt ccaacattga  2760
cttttcttcat cactgcaaca tttctctgac tagcaatgtg acgatgtaac aaatgagatt  2820
ttctcatttta ataataaaa  agttgtgtaa tgttttgc                         2858
```

<210> SEQ ID NO 6
<211> LENGTH: 473
<212> TYPE: PRT
<213> ORGANISM: Homo sapiens

<400> SEQUENCE: 6

```
Met Ala Gln His Asp Phe Ala Pro Ala Trp Leu Asn Phe Pro Thr Pro
1               5                   10                  15

Pro Ser Ser Thr Lys Ser Ser Leu Asn Phe Glu Lys His Ser Glu Asn
            20                  25                  30

Phe Ala Trp Thr Glu Asn Arg Tyr Asp Val Asn Arg Arg His Asn
        35                  40                  45

Ser Ser Asp Gly Phe Asp Ser Ala Ile Gly Arg Pro Asn Gly Gly Asn
    50                  55                  60

Phe Gly Arg Lys Glu Lys Asn Gly Trp Arg Thr His Gly Arg Asn Gly
65                  70                  75                  80

Thr Glu Asn Ile Asn His Arg Gly Gly Tyr His Gly Gly Ser Ser Arg
                85                  90                  95

Ser Arg Ser Ser Ile Phe His Ala Gly Lys Ser Gln Gly Leu His Glu
            100                 105                 110

Asn Asn Ile Pro Asp Asn Glu Thr Gly Arg Lys Glu Asp Lys Arg Glu
        115                 120                 125

Arg Lys Gln Phe Glu Ala Glu Asp Phe Pro Ser Leu Asn Pro Glu Tyr
130                 135                 140

Glu Arg Glu Pro Asn His Asn Lys Ser Leu Ala Ala Gly Val Trp Glu
145                 150                 155                 160

Tyr Pro Pro Asn Pro Lys Ser Arg Ala Pro Arg Met Leu Val Ile Lys
                165                 170                 175

Lys Gly Asn Thr Lys Asp Leu Gln Leu Ser Gly Phe Pro Val Val Gly
            180                 185                 190

Asn Leu Pro Ser Gln Pro Val Lys Asn Gly Thr Gly Pro Ser Val Tyr
        195                 200                 205

Lys Gly Leu Val Pro Lys Pro Ala Ala Pro Thr Lys Pro Thr Gln
    210                 215                 220

Trp Lys Ser Gln Thr Lys Glu Asn Lys Val Gly Thr Ser Phe Pro His
225                 230                 235                 240

Glu Ser Thr Phe Gly Val Gly Asn Phe Asn Ala Phe Lys Ser Thr Ala
                245                 250                 255

Lys Asn Phe Ser Pro Ser Thr Asn Ser Val Lys Glu Cys Asn Arg Ser
            260                 265                 270

Asn Ser Ser Ser Pro Val Asp Lys Leu Asn Gln Gln Pro Arg Leu Thr
        275                 280                 285

Lys Leu Thr Arg Met Arg Thr Asp Lys Lys Ser Glu Phe Leu Lys Ala
    290                 295                 300

Leu Lys Arg Asp Arg Val Glu Glu Glu His Glu Asp Glu Ser Arg Ala
305                 310                 315                 320

Gly Ser Glu Lys Asp Asp Asp Ser Phe Asn Leu His Asn Ser Asn Ser
                325                 330                 335

Thr His Gln Glu Arg Asp Ile Asn Arg Asn Phe Asp Glu Asn Glu Ile
            340                 345                 350

Pro Gln Glu Asn Gly Asn Ala Ser Val Ile Ser Gln Gln Ile Ile Arg
        355                 360                 365

Ser Ser Thr Phe Pro Gln Thr Asp Val Leu Ser Ser Leu Glu Ala
    370                 375                 380
```

-continued

```
Glu His Arg Leu Leu Lys Glu Met Gly Trp Gln Glu Asp Ser Glu Asn
385                 390                 395                 400

Asp Glu Thr Cys Ala Pro Leu Thr Glu Asp Glu Met Arg Glu Phe Gln
            405                 410                 415

Val Ile Ser Glu Gln Leu Gln Lys Asn Gly Leu Arg Lys Asn Gly Ile
        420                 425                 430

Leu Lys Asn Gly Leu Ile Cys Asp Phe Lys Phe Gly Pro Trp Lys Asn
        435                 440                 445

Ser Thr Phe Lys Pro Thr Thr Glu Asn Asp Asp Thr Glu Thr Ser Ser
    450                 455                 460

Ser Asp Thr Ser Asp Asp Asp Val
465                 470
```

<210> SEQ ID NO 7
<211> LENGTH: 27
<212> TYPE: DNA
<213> ORGANISM: Artificial
<220> FEATURE:
<223> OTHER INFORMATION: 5' primer for primary RACE

<400> SEQUENCE: 7
caggctggag caaagtcatg ctgcgcc                                      27

<210> SEQ ID NO 8
<211> LENGTH: 28
<212> TYPE: DNA
<213> ORGANISM: Artificial
<220> FEATURE:
<223> OTHER INFORMATION: 5' primer for secondary RACE

<400> SEQUENCE: 8
aggtccagtc tctccaactc agtgaaac                                     28

<210> SEQ ID NO 9
<211> LENGTH: 26
<212> TYPE: DNA
<213> ORGANISM: Artificial
<220> FEATURE:
<223> OTHER INFORMATION: 3' primer for primary RACE

<400> SEQUENCE: 9
ctgatctgtg acttcaagtt tggacc                                       26

<210> SEQ ID NO 10
<211> LENGTH: 29
<212> TYPE: DNA
<213> ORGANISM: Artificial
<220> FEATURE:
<223> OTHER INFORMATION: 3' primer for secondary RACE

<400> SEQUENCE: 10
tgacgatgtg tgaaggagat cctcacagc                                    29

<210> SEQ ID NO 11
<211> LENGTH: 10
<212> TYPE: DNA
<213> ORGANISM: Artificial
<220> FEATURE:
<223> OTHER INFORMATION: Sp1 binding consensus motif probe

<400> SEQUENCE: 11
tgggcgggc                                                          10

```
<210> SEQ ID NO 12
<211> LENGTH: 273
<212> TYPE: DNA
<213> ORGANISM: Homo sapiens

<400> SEQUENCE: 12
ctaacctgat tggtttattc aaacaaaccc cggccaactc agccgttcat aggtggatat      60
aaaaggcaag ctacgattgg ttcttctgga cggagacggt gagagcgact cagggattgg    120
ctggtctgct tcgggcgggc taaaggaagg ttcaagtcga gctctcctaa ccgacgcgcg    180
tctgtggaga agcggcttgg tcggggtgg tctcgtgggg tcctgcctgt ttagtcgctt     240
tcagggttct tgagcccctt cacgaccgtc acc                                 273

<210> SEQ ID NO 13
<211> LENGTH: 239
<212> TYPE: DNA
<213> ORGANISM: Mus musculus

<400> SEQUENCE: 13
tccgggaaat gcgcgccaga gttgcaggcg gggggggggg gggggggcgg ggccgtggct      60
ccggaaggcg gggtctctct gtgggcgtag cgtgggcggg gctgtgccgg ggcagcccgg    120
taaaaaagag cgtggcgggc cgcggtctct gagagccatc gggaagcgac cctgccagcg    180
agccaacgca gacccagaga gcttcggcgg agagaaccgg gaacacgctc ggaaccatg     239
```

DNA ENCODING G+C-RICH PROMOTER BINDING PROTEIN

CROSS REFERENCE TO RELATED APPLICATIONS

This application is a divisional of U.S. application Ser. No. 10/947,997, filed Sep. 22, 2004, (now U.S. Pat. No. 7,368,538), which is a continuation-in-part of International Application No. PCT/US03/07870, filed Mar. 17, 2003, which claims priority to U.S. Provisional Application No. 60/366,898, filed Mar. 22, 2002. All of the above priority documents are incorporated herein by reference in their entirety.

BACKGROUND OF THE INVENTION

1. Field of the Invention

The present invention is generally related to the modulation of transcription. More specifically, the present invention is related to the regulation of genes controlled by G+C-rich promoters.

2. Description of Related Art

Promoters that govern the transcription of mammalian genes by RNA polymerase II fall broadly into three types: the classical TATAAA-box-dependent promoters, the initiator element (Inr)-dependent promoters, and the G+C-rich promoters which also have been referred to as CpG islands. Transcription initiation at the TATAAA-box-dependent promoters is dictated by the direct interaction of the TATAAA-box with the TATA-binding protein TBP as a first and rate-limiting step (reviewed by Buratowski et al., 1989). Likewise, transcription initiation at Inr-dependent promoters occurs when the Inr element interacts with sequence-specific Inr-binding proteins (Smale & Baltimore, 1989, Smale et al., 1990). The mechanism by which transcription initiation sites within G+C-rich promoters are recognized by the RNA Polymerase II transcription machinery is currently unelucidated.

Transcription initiation of a large number of mammalian genes, including most housekeeping genes, and many highly regulated genes controlling cell growth and differentiation, is under the control of G+C-rich promoters (Rauth et al., 1989). This class of promoter is not found in either the *drosophila* or yeast genomes. Because a common characteristic of this type of promoter is the presence of a non-canonical TATAAA box and one or more Sp1 binding sites upstream of the major transcription initiation site, several reports have claimed that those sequences are the key functional elements in G+C-rich promoters (Blake et al., 1990, Innis et al., 1991). However, reports that challenged these claims, in some cases even with respect to the same promoter, also have been published (Means & Farnham, 1990a, 1990b, Ackerman et al., 1993). The lack of obvious conserved sequence motifs shared among different G+C-rich promoters, with the exception of the Sp1 binding sites and the "non-canonical" TATAAA boxes, provides further impetus for investigations to elucidate how transcription can initiate non-randomly at these precise genome locations.

SUMMARY OF THE INVENTION

The present invention is related to an isolated DNA encoding a GPBP polypeptide. The encoded polypeptide may comprise the sequence set forth in SEQ ID NO:2, SEQ ID NO:4 or homologs thereof. The DNA may comprise the sequence set forth in SEQ ID NO:1 or SEQ ID NO:3. The encoded polypeptide may specifically bind to a G+C-rich promoter, which may be MSPE. The present invention is also related to an isolated GPBP polypeptide.

The present invention is also related to a vector comprising a DNA encoding a GPBP polypeptide. The DNA encoding a GPBP polypeptide may be operative linked to a control group. The vector may be an expression vector.

The present invention is also related to an antibody that specifically binds to a GPBP polypeptide. The antibody may be a monoclonal antibody or polyclonal antibody. The antibody may also be a single chain antibody or a humanized antibody.

The present invention is also related to a method of detecting altered expression of GPBP. A sample to be tested is contacted with an antibody that specifically binds to a GPBP polypeptide. The binding of the antibody to the sample is measured and compared to a control. Altered expression of GPBP is identified by a difference in binding of antibody to the sample and the control. The present invention is also related to a method of diagnosing cancer by detecting the altered expression of GPBP.

The present is also related to a method of modulating the stability of a DNA nanostructure comprising adding a GPBP polypeptide to the nanostructure.

BRIEF DESCRIPTION OF THE DRAWINGS

FIGS. 1A-1B show the sequence of mGPBP and sequence homology. FIG. 1A shows the complete cDNA sequence corresponding to the 3.0-kb murine GPBP mRNA (SEQ ID NO:1), including the deduced amino acid sequence encoded by the ORF (SEQ ID NO:2) (GenBank accession number AY382529). FIG. 1B shows sequence small regional sequence homology (open boxes) of the ORF (solid box) on the amino acid sequence level with yeast TFIIFα subunit (TFIIFα), yABF-1, murine SSRP (mHMG-1 like) and helicases.

FIG. 3 shows that mammalian GPBP is approximately 66 kd in size and is ubiquitously expressed. Panel A, Lanes 1-5 displayed electrophoretically separated proteins in SDS polyacrylamide gels stained with Coomassie Blue. Bacterial lysate derived a BL21 strain carrying the PET-mGPBP expression plasmid were analyzed either without (−) or with (+) IPTG induction. Lane 4 displayed purified recombinant mGPBP. Molecular weight markers are shown in lanes 1 and 5. The samples used in lanes 3 and 4 were also analyzed by Western blotting using antiserum against mGPBP as probe in lanes 7 and 8, respectively. Control BL21 cell (without the PET-mGPBP expression plasmid) lysate was analyzed in lane 6. Panel B shows the Western blot analyses of cell lysates derived from human HeLa cells (lane 1), mouse C1-1D cells (lane 2), human JEG-3 cells (lane 3), human VA-2 cells (lane 4), mouse M2-10B4 cells (lane 5), and human 293 cells (lane 6) using the anti-mGPBP antiserum as probe.

FIG. 4 shows that the purified recombinant mGPBP can bind specifically to the mouse ADA gene's G+C-rich promoter in EMSA. The DNA probe 4C' used in panel A is 4 copies of the MSPE C' that had been end-ligated. Purified rmGPBP binds specifically to the probe and caused a shift in probe electrophoretic mobility from the free probe location (lane 1) to the bound probe location (lane 2). This binding can be specifically competed out by adding 35-fold (lane 3) and 175-fold (lane 4) excess unlabeled probes, but cannot be competed out by adding similar amounts of unlabeled E2F binding motifs (lanes 5 and 6) or a 200 bp plasmid sequence (lanes 7 and 8). A single copy of this fragment C' in the context of the labeled 236 bp mouse ADA gene promoter can also bind to and be electrophoretically retarded by the purified rmGPBP (Panel B, lanes 1 and 2). This binding can be competed out by excess unlabeled probe (lanes 3 and 4) or the 4C' probed used in panel A (lanes 5 and 6). This binding is again not competed out by unlabeled E2F binding sequences (lanes 7 and 8) or the 200 bp plasmid sequences (lanes 9 and 10).

FIGS. 8A-8B show the complete cDNA sequence of human GPBP (SEQ ID NO:3), including the deduced amino acid sequence encoded by the ORF (SEQ ID NO:4).

FIG. 9 shows that the TATA box contained the Topo IIα gene's G+C-rich promoter binds specifically to mGPBP but is only partially dependent on its presence for promoter function. (A) The human Topo IIα gene promoter (SEQ ID NO:12) shows no obvious sequence homology to the MSPE within the Ada gene promoter (SEQ ID NO:13). The sequences displaying an imperfect dyad symmetry flanking the major transcription initiation site (arrow) are underlined. The consensus TATA element in the Topo IIα gene promoter is boxed. (B) Electrophoretic mobility of the $^{32}$P-labeled Topo IIα gene promoter probe (lane 1, arrow) was retarded (bound probe) by the presence of purified recombinant mGPBP (lane 2). This retardation of the probe can be reversed by competition with excess unlabeled probe (lanes 3 and 4) or linked quadruple copies of the MSPE derived from the Ada gene promoter (lanes 7 and 8), but not by excess copies of a 200-bp plasmid sequence that shows no secondary conformational changes under negative superhelicity (lanes 5 and 6). (C) In vitro transcription of supercoiled reporter genes driven by the Topo IIα gene promoter with HeLa nuclear extract was partially suppressed by the presence of anti-GPBP antibodies but was unaffected by the presence of preimmune antibodies. The suppressive effect of the anti-GPBP antibodies can be fully reversed by the addition of 20 ng of purified recombinant mGPBP to the reaction mixture. The statistical significance (P) for the difference of transcription levels in the absence and presence of anti-mGPBP antibodies (*) was found by a paired Student t test to be <0.000003 (n=5), and P for the difference of transcription levels in the presence of the anti-mGPBP antibodies with and without additional recombinant mGPBP (+) was found by a paired Student t test to be <0.028 (n=5).

DETAILED DESCRIPTION

G+C-rich promoters control the transcription initiation of many mammalian genes, including most housekeeping and Central Nervous System (CNS) genes, and many highly regulated genes that control cell growth and differentiation (Melton et al., 1984, McGrogan et al., 1985, Kreidberg & Kelly, 1986, Rauth et al., 1989, Sehgal et al., 1988, Ackerman et al., 1993). Except for the presence of a non-canonical TATAAA box and one or more Sp1 binding sites, there is no obvious sequence homology that is shared among the many G+C-rich promoters that have been analyzed. The murine ADA gene's G+C-rich promoter exhibits all the typical features of this class of promoter. We have previously noted that the murine ADA gene's MSPE shares no significant sequence homology with other G+C-rich promoters, including that of the human ADA gene (Ackerman et al., 1993). Our group also demonstrated that neither the non-canonical TATAAA motif (TAAAAAA) nor the Sp1 binding sites are required for basal promoter activity (Ackerman et al. 1993). More recently, we have shown that this TAAAAAA sequence is also not required for this promoter to respond to the ADA gene's T-cell specific enhancer (Hsu et al., submitted). It is therefore unclear what signaling molecules or DNA sequences are required for RNA polymerase II transcription initiation to occur non-randomly at these precise G+C-rich promoter locations within the mammalian genome.

Figure 2:
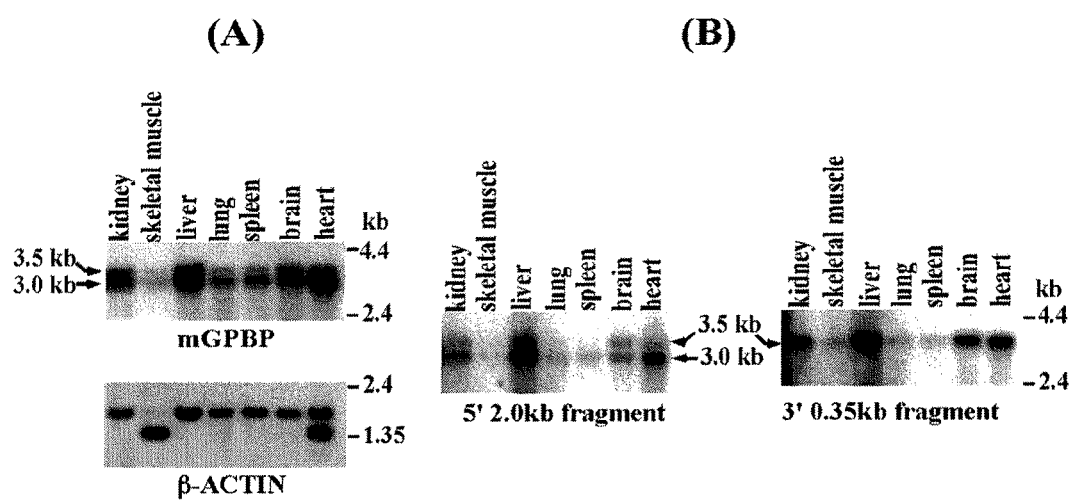
FIG. 2 shows northern blot analyses to examine the murine GPBP mRNA species and tissue distribution. Approximately 3 µg of poly A⁺ RNA derived from the tissues indicated was loaded per lane. The blot shown in panel A was first probed with a mGPBP specific probe (upper panel), stripped, and reprobed with a β-actin probe (bottom panel). In panel B, the blot was probed with a 2.0 kb probe derived from the 5' terminus of the mGPGP cDNA (left panel), stripped, and reprobed with a 350 bp probe derived from the 3' terminus of the mGPBP cDNA corresponding to the 3.5 kb mGPBP mRNA (right panel). The 5' probe hybridized with both mRNA species, whereas the 3' probe hybridized with only the 3.5 kb mRNA.

The search for a DNA binding factor that can recognize a small DNA binding motif within a G+C-rich promoter and initiate the assembly of the transcription initiation complex has been the subject of intensive but, as yet, unfruitful investigation (Lichtsteiner et al., 1987, Sopta et al., 1989, Means & Farnham, 1990a). Our work on the murine ADA gene's G+C-rich promoter has established that this promoter has neither a functional TATAAA-box nor a potential initiator element that is larger than 4 bp (Ackerman et al., 1993; Hsu et al., submitted). Instead, the minimal self-sufficient promoter activity resides within a 48 bp MSPE whose sequence displays an imperfect dyad symmetry with theoretical secondary structure-forming potential. DNA sequences with the theoretical potential to form similar structures have also been found in many other G+C-rich promoters (Ackerman et al., 1993). More recently, we have shown that this MSPE can adopt a non-B-form DNA secondary structure under negative-superhelical torsion condition that approximates that found in physiological chromatin (Hsu et al., submitted). Since we previously had demonstrated that the ADA gene's MSPE contains nuclear protein binding sites (Ackerman et al., 1993), this DNA element was used to isolate a cloned nuclear protein that can bind both to the promoter and to key proteins that participate in the assembly of the RNA polymerase II transcription initiation complex. Our success in this endeavor may owe much to our choice of using this rather large MSPE as the probe. This MSPE does not depend on other proximal activator motifs such as Sp1 binding sites to exhibit promoter function (Ackerman et al., 1993). Smaller elements within the MSPE do not suffice as self-sufficient promoters (Ackerman et al., 1993, and Ackerman & Yeung, unpublished data). By using a multimerized MSPE probe, we successfully identified a λgt11 phage cDNA expression clone that encodes a G+C-rich Promoter Binding Protein (GPBP). Full-length cDNA clones corresponding to the two cross-hybridizing mRNA species, as determined by Northern blot analysis (FIG. 2), were generated using 5' and 3' RACE. These 2 mRNA species apparently differ only in their 3' polyadenylation site utilization, and they both contain an identical 1,479 nt Open Reading Frame (ORF) 1.15 kb downstream of the transcription initiation site. The extremely high nucleotide sequence conservation between the 5' and 3' UTRs of the mouse and human GPBP genes (FIGS. 8A-8B) suggests that these UTR sequences have important functional roles.

Figure 1B:
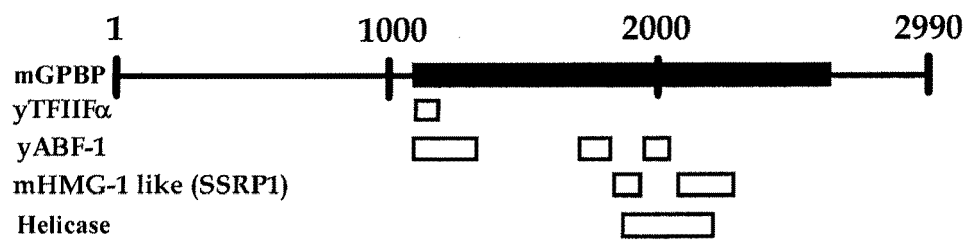

Because G+C-rich promoters are present upstream of many essential mammalian housekeeping genes, but are not found in either the yeast or *drosophila* genomes, we predicted that if GPBP expression is critical to transcription from G+C-rich promoters, it would be ubiquitously expressed in mammalian cells and be absent from both yeast and *drosophila* genomes. Northern (FIG. 2) and Western (FIG. 3B) blot analyses of various mouse tissues and mammalian cell lines confirmed the former prediction. A sequence homology search of the DNA sequence database (which includes the entire yeast and *drosophila* genome sequences) revealed no obvious mGPBP orthologs in any of the non-mammalian genomes, although small domain-specific homologies to a number of transcription factors were found (FIG. 1B). The domain-specific homology to the SSRP1 gene (FIG. 1B) is particularly intriguing. Since SSRP1 is known to bind DNA in a DNA structure-dependent manner (Shirakata et al., 1991, Bruhn et al., 1992), it is possible that GPBP may also share that unusual property and bind to MSPE via structural recognition.

Surprisingly, although no obvious mGPBP orthologs were uncovered by the sequence search, the murine ADA gene's G+C-rich promoter does function when it is introduced into yeast cells (data not shown). We note with interest that yeast ABF-1, which shares some domain-specific homology with mGPBP (FIG. 1B), can reportedly transactivate the yeast TRP3 gene promoter which possesses a "suboptimal" TATA-box (Martens & Brandl, 1994). Because yeast origins of replication do not function as such in mammalian cells and no one has been able to identify a mammalian yABF-1 ortholog by low-stringency hybridization screening, yABF-1's ability to transactivate a yeast gene promoter with a non-canonical TATA-box and its shared sequence homology with certain mGPBP domains raises the possibility that yABF-1 and mGPBP may share similar cellular functions but recognize and bind to highly divergent DNA sequences. It is certainly formally possible that yABF1, which has no known mammalian orthologs, may also promote transcription at the mouse ADA gene's G+C-rich promoter in mGPBP-deficient yeast cells.

The predicted size of mGPBP based on the cDNA ORF sequence was confirmed by Western blot analysis of lysates of various mammalian cell lines derived from diverse tissues of origin (FIG. 3). The other immuno-cross-reacting proteins seen in all cell lysates (FIG. 3B) may be either degradation products of mammalian GPBP or other members of a GPBP gene family. We have also cloned the human GPBP ortholog (FIGS. 8A-8B) and found that it contained an ORF that shares 93% homology at the nucleotide level (and 95% identity in the predicted amino acid sequence) with the mouse GPBP ORF. The presence of an extremely well-conserved GPBP gene in the mouse and human genomes and the absence of an ortholog gene identifiable by sequence homology in the yeast and *drosophila* genomes suggest that the GPBP gene may be one of the very rare mammal—(or higher eukaryote—) specific genes. This observation is consistent with the observation that while mammalian genomes possess numerous G+C-rich promoters, no such promoters have been reported in either the yeast or *drosophila* genome.

Purified recombinant mGPBP was shown to bind specifically to the murine ADA gene's MSPE in EMSA in the absence of any other mammalian proteins. In the screening of the cDNA library and in EMSA, a probe consisting of 4 copies of the 48 bp MSPE (C') [which differs from fragment C by only the terminal nucleotide at each end] end-ligated into a single 200 bp probe binds specifically to recombinant mGPBP. The specificity of the binding reaction was demonstrated in competition EMSAs using specific and non-specific competitor DNA (FIG. 4A). Interestingly, a single copy C or C' probe, which cannot maintain a potential double stranded 4-way junction because of the lack of additional complementary sequences flanking the potential stem-and-loop structure (Ackerman et al., 1993) did not bind GPBP in similar EMSA experiments (data not shown). However, the 236 bp mouse ADA gene promoter with its single copy of the MSPE effectively and specifically bound to the recombinant mGPBP (FIG. 4B). The mGPBP binding interaction was specific to the MSPE, since this binding can be competed out by excess amounts of the 4C' fragment, but not by a similar excess of non-specific DNA sequences. These results thus established that purified recombinant mGPBP can specifically and directly bind to the murine ADA gene promoter's G+C-rich MSPE in the absence of any other transcription factors. This observation is consistent with GPBP potentially being responsible for mediating the initial assembly of the transcription initiation complex. This GPBP/DNA interaction cannot be due to junction sequence artifacts, since probes (such as C, C', and the entire promoter) consisting of MSPE with different flanking sequences all bind effectively and specifically to the protein. Interestingly, optimal electrophoretic mobility shift of the mGPBP-bound MSPE-containing probes occurred in EMSAs performed in 1× TBE instead of the standard lower 0.5× TBE salt conditions (FIG. 4, and data not shown). The higher salt condition should favor the maintenance of DNA double-strandedness in the MSPE flanking sequences and/or the imperfectly matched potential stem sequence described by Ackerman et al., 1993, and stabilize the unusual non-B form DNA secondary structure that may be required for mGPBP binding.

Figure 5:
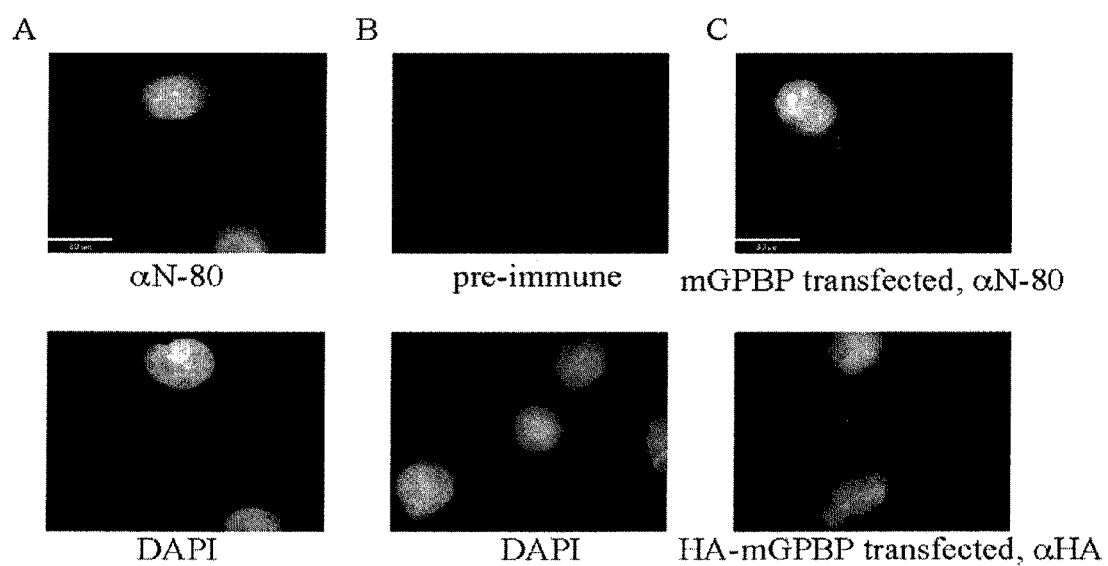
FIG. 5 shows that both human and transfected mGPGP are localized in the nucleus. Human HeLa cells were stained with antibody against mGPBP (N80) (panel A top) or from preimmune serum (panel B top). The location of the nucleus was determined by counterstaining the cells with DAPI (panels A&B bottom). The transfected HA-tagged mGPBP was localized in panel C using the N80 (panel C top) and anti-HA antibody (panel C bottom).

In situ binding assays using anti-mGPBP antiserum as a probe demonstrated that endogenous human GPBP is nuclear-localized in HeLa cells (FIG. 5A). The nuclear-localization property of the mGPBP was confirmed by transfecting HA-tagged mGPBP expression vectors into the HeLa cells and detecting the transduced HA tag in the cell nuclei using anti-HA antibodies (FIG. 4C). These results are consistent with GPBP's proposed role as a mediator of transcription initiation complex assembly at the promoter, a role which would require nuclear-localization.

Western blot analysis of mouse C1-1D cell nuclear extract proteins that either complex with immobilized mGPBP or are co-immunoprecipitated with HA-tagged mGPBP expressed in intact cells revealed that mGPBP can complex specifically with TBP, TFIIB, TFIIF, RNA polymerase II, and P300/CBP both in vitro and in vivo. In contrast, the nucleoporin p62 protein, which is present in nuclear extract but does not participate in transcription complex formation, did not complex with mGPBP in the same assays. Since all these mGPBP-associated transcription initiation factors are known to participate in the formation of the RNA polymerase II transcription initiation complex (Buratowski et al., 1989, Chan & La Thangue, 2001), these observations are consistent with the proposed role of GPBP as a mediator of transcription initiation complex assembly, following its binding to G+C-rich promoters.

Figure 7:
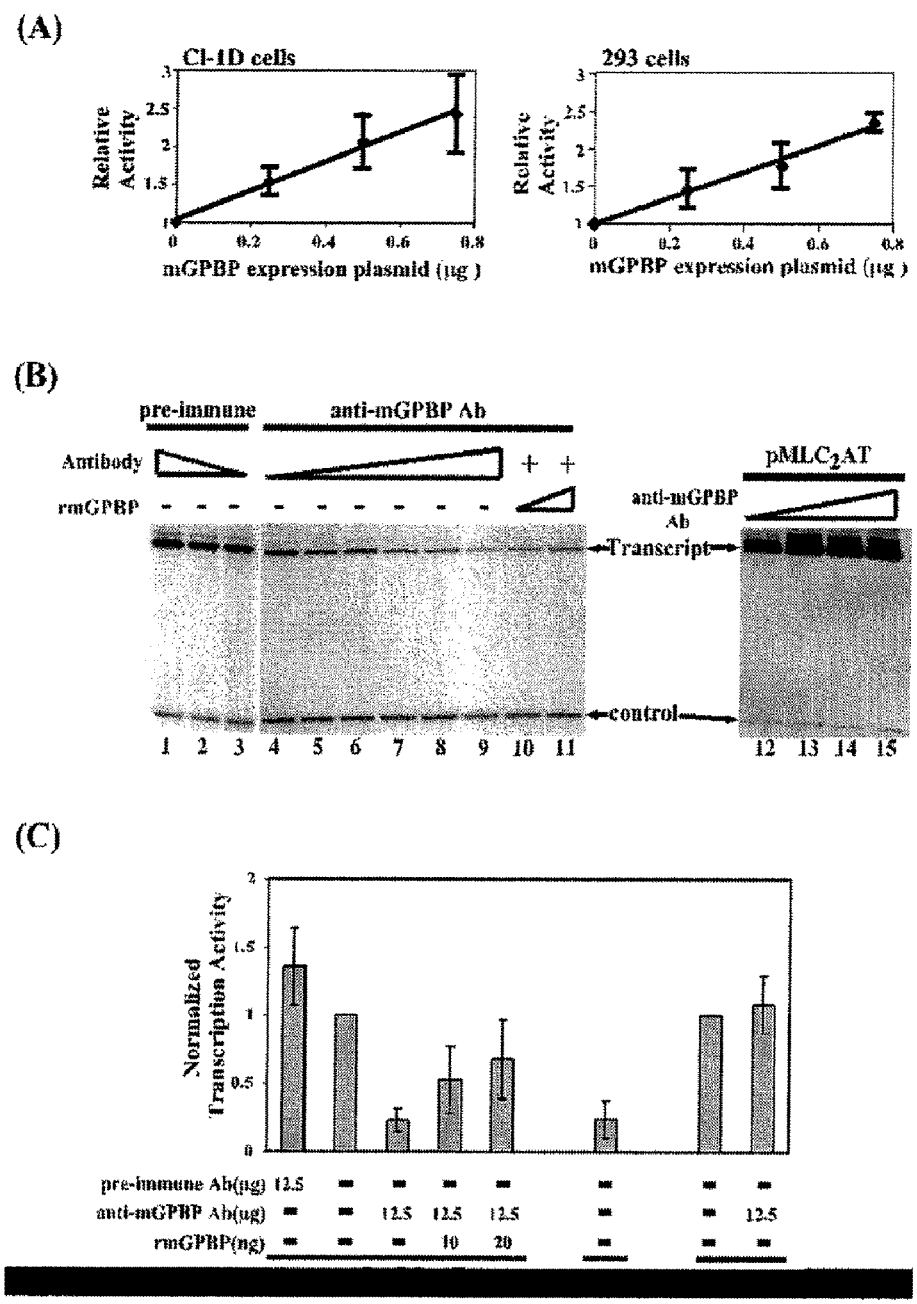
FIG. 7 shows that mGPBP is specifically required for transcription initiated at the mouse ADA gene's G+C-rich promoter. Co-transfection of a mouse ADA gene promoter controlled luciferase reporter gene construct together with increasing amounts of a mGPBP expression vector into either mouse C1-1D cells or human 293 cells resulted in a linear increase in reporter gene activity (Panel A). In vitro transcription assays performed by co-incubation of a supercoiled mouse ADA gene promoter controlled G-less cassette reporter gene with human mouse C1-1D cell nuclear extracts showed that reporter transcript (Transcript) production was unaltered by the addition of increasing amounts of pre-immune serum derived antibodies (lanes 1-3, Panel B). In contrast, increasing amounts of anti-mGPBP antibodies caused a gradual decrease in reporter transcript production (lanes 4-9, Panel B). This immuno-suppression effect can be reversed by the addition of purified rmGPBP (lanes 10 and 11, Panel B). Transcription of the G-less cassette reporter gene under the control of the TATAAA-box dependent adeno-virus major late promoter was not affected by the addition of anti-mGPBP antibodies (lanes 12-15, Panel B). The assay results were repeated at least 3 times and the normalized quantitation of the transcription assay results (using a phosphorimager), together with standard deviations of multiple repetitions are shown in graphic form in panel C.

In co-transfection assays, mGPBP was found to trans-activate the murine ADA gene's G+C-rich promoter (FIG. 7A) in the two different cell lines (C1-1D and 293) used. Because all mammalian cells tested contain significant levels of endogenous GPBP (FIG. 3B), it is not surprising that the transactivating effect of the exogenous recombinant mGPBP in the transfected cells is only in the 2.5-fold range. More significantly, in the presence of high copy numbers of the co-transfected reporter gene in both C1-1D and 293 cells, the trans-activating effect of the mGPBP expression vector remained linear over the >8-fold range of levels of GPBP expression vector used (FIG. 7A). Thus, in the presence of an excess G+C-rich promoter sequences in the cell, GPBP appeared to be rate limiting for reporter gene transcription. Moreover, GPBP activity was shown to be essential for transcription directed by the mouse ADA gene's G+C-rich promoter. In in vitro transcription assays, sequestering of GPBP in human HeLa cell nuclear extract by immunoabsorption caused a proportional and ultimately complete suppression of transcription from the ADA gene's G+C-rich promoter (with the level of transcription declining to levels indistinguishable from that from a promoterless reporter construct (FIGS. 7B&C). This suppression was reversed by replenishing the GPBP-depleted nuclear extract with purified recombinant mGPBP (FIGS. 7B&C). More recently, this finding of GPBP dependence for transcriptional activity has been extended to the only additional G+C-rich promoter tested (Yeung et al., unpublished data). This promoter shared no sequence homology with the murine ADA gene's MSPE, but showed a similar secondary DNA structure forming potential (Ackerman et al., 1993), and can also bind purified recombinant mGPBP in EMSA experiments similar to those shown for the ADA gene's G+C-rich promoter (FIG. 4B). Additionally, six other additional mammalian G+C-rich promoters tested all showed a similar capacity to bind purified recombinant GPBP (Yeung et al., unpublished data). All these other G+C-rich promoters examined also displayed similar degrees of DNA sequence diversity and DNA secondary structure forming potential similarity comparable to the murine ADA gene promoter's MSPE (Ackerman et al., 1993, and Yeung et al., unpublished data). These observations thus extend our mouse ADA gene promoter-based model and strongly support a proposed role for GPBP as a general transcription factor that can bind multiple mammalian G+C-rich promoters and mediate the assembly of transcription initiation complexes at these promoters.

In striking contrast to the G+C-rich promoter's requirement for GPBP in the in vitro transcription assay, transcription activity from the adenovirus major late gene's classical TATAAA-box dependent promoter was totally unaffected by the immunoabsorption mediated sequestering of GPBP in the HeLa cell nuclear extract (FIGS. 7B&C). These results established that GPBP is only required for transcription initiated at the G+C-rich promoter, but is totally dispensable for transcription initiated at a classical TATAAA-box dependent promoter. The observed linearity of GPBP's transactivation effect (FIG. 7A) and its absolute requirement in G+C-rich promoter-directed transcription (FIG. 7C) are both consistent with the predicted role of GPBP as a rate-limiting factor for transcription initiated at a G+C-rich promoter.

Recently (Trembley, J. H. et al., 2002), the same in vitro transcription assays (with the same reporter constructs described above as templates) were used to examine transcription elongation suppression caused by immunoabsorption of a factor that associates with members of each of the three various classes (Conaway et al, 2000) of transcription elongation complexes. In contrast to the results described for the immunoabsorption of GPBP, transcript production from both the G+C-rich and TATAAA-dependent promoters was similarly inhibited by the addition of antibodies directed against that proposed transcription elongation factor (Trembley, J. H. et al., in press). This observation suggests that elongation of transcripts initiated at both G+C-rich and TATAAA-dependent promoters may utilize common elongation complexes, and implicate the differential transcription inhibitory effects displayed by GPBP-sequestering as interference against a different transcription-associated process. Since GPBP can bind to a G+C-rich promoter's MSPE, can associate with all the known transcription initiation assembly factors tested, and is functionally required for transcription initiated at that promoter, the anti-GPBP antibodies had probably interfered with a TATAAA-box independent transcription initiation complex assembly step. Whether these anti-mGPBP antibodies would interfere with transcription at non-G+C-rich, TATA-box deficient initiator-element dependent promoters and whether GPBP is similarly required for transcription initiated at all mammalian G+C-rich promoters remain unresolved questions that have now become tractable with the new reagents we now have on hand.

These results thus describe the discovery of a novel requisite promoter-specific transactivating transcription factor with demonstrable abilities to both bind a typical G+C-rich promoter and interact with multiple transcription factors that comprise the core mammalian RNA polymerase II transcription initiation complex. Since GPBP is not required for transcription directed by the adenovirus major late gene's classical TATAAA-box-dependent promoter, the results also provide definitive proof that transcription initiated at the murine ADA gene's G+C-rich promoter is mechanistically distinct from that initiated at a classical TATAAA-box-dependent promoter.

1. Definitions

As used herein, the term "analog", when used in the context of a peptide or polypeptide, means a peptide or polypeptide comprising one or more non-standard amino acids or other structural variations from the conventional set of amino acids, and when used in the context of nucleic acids means a nucleic acid comprising one or more non-standard nucleotides or other structural variations from the conventional set of nucleotides.

As used herein, the term "derivative", when used in the context of a peptide, polypeptide, or nucleic acid means a peptide, polypeptide or nucleic acid different other than in primary structure (amino acids, amino acid analogs, nucleotides and nucleotide analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, radiolabelled peptides, polypeptides or nucleic acids, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

As used herein, the term "fragment", when used in the context of a peptide or polypeptide, means a peptide of from about 8 to about 50 amino acids in length. The fragment may be 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length. When used in the context of a nucleic acid, "fragment" means a nucleic acid of from about 5 ti about 50 nucleotides in length. The fragment may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length.

As used herein, the term "homolog", when used in the context of a peptide, polypeptide, or nucleic acid means a peptide, polypeptide or nucleic acid sharing a common evolutionary ancestor.

As used herein, the term "variant", when used in the context of a peptide or polypeptide, means a peptide or polypeptide that differs in amino acid sequence by the insertion, deletion, or conservative substitution of amino acids, but retain at least one biological activity. When used in the context of a nucleic acid, "variant" means a nucleic acid that differs in nucleotide sequence by the insertion, deletion, or conservative substitution of nucleotides, but is able to hybridize to a sequence encoding GPBP, or complement thereof, under stringent conditions. For purposes of the present invention, "biological activity" includes, but is not limited to, the ability to be bound by a specific antibody.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., *J. Mol. Biol.* 157: 105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, which is incorporated herein by reference. Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Additionally, computerized algorithms are available to assist in predicting amino acid sequence domains likely to be accessible to an aqueous solvent. These domains are known in the art to frequently be disposed towards the exterior of a peptide, thereby potentially contributing to binding determinants, including antigenic determinants.

2. GPBP

The present invention provides GPBP-related materials and methods. GPBP polypeptides may bind to a G+C-rich promoter. A representative example of a G+C-rich promoter includes, but is not limited to, MSPE Representative examples of GPBP include, but are not limited to, murine GPBP and human GPBP. GPBP includes vasculin (SEQ ID NO:6), as disclosed by Bijnens et al. (2003). Vasculin is identical to human GPBP, except for a 60 nucleotide exon that is missing in vasculin. The missing 60 nucleotides in the cDNA encoding vasculin may be identified by aligning SEQ ID NO:3 and SEQ ID NO:5.

a. Nucleic Acids

The present invention is related to nucleic acids encoding GPBP, as well as fragments, analogs, homologs and derivatives thereof. The nucleic acid may be DNA or RNA, single- or double-stranded, and may be may purified and isolated from a native source, or produced using synthetic or recombinant techniques known in the art.

The present invention is also related to vectors comprising the nucleic acid. The vector may be an expression vector. The expression vectors may be designed for expression of the polypeptide in prokaryotic or eukaryotic cells. The nucleic acid may be operative linked to a control region, which may regulate expression of the polypeptide. Representative examples of inducible expression systems are disclosed in Sambrook et al., Molecular Cloning, which is incorporated herein by reference.

The present invention is also related to host cells transformed or transfected with the vector. Representative host cells are discussed in Goeddel, *Gene Expression Technology: Methods in Enzymology* 185, Academic Press, San Diego, Calif. (1990), the contents of which are hereby incorporated in their entirety.

b. Polypeptides

The present invention is also related to GPBP polypeptides, as well as fragments, analogs, homologs, variants and derivatives thereof. The polypeptides may be native or recombinant.

The present invention is also related to methods of making the polypeptide. The polypeptide may be made by a method comprising expressing a nucleic acid encoding the polypeptide in a suitable host cell and purifying the polypeptide. Methods for the optimization of protein expression in host cells are discussed further in Hannig et al., Trends Biotechnol., 16(2):54-60 (1998), the contents of which are hereby incorporated by reference in their entirety. Other methods for making the polypeptide use techniques that are known in the art, such as the isolation and purification of native polypeptides or the use of synthetic techniques for polypeptide production.

c. Antibodies

The present invention is also related to antibodies that specifically bind to GPBP. The antibodies may be produced using techniques known in the art. The antibody may be of classes IgG, IgM, IgA, IgD or IgE, or fragments or derivatives thereof, including Fab, F(ab')$_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody, CDR-grafted antibody, "humanized" antibody, and other antibody forms known in the art. The antibody may be derivatized by the attachment of one or more chemical, peptide, or polypeptide moieties known in the art. The antibody may be conjugated with a chemical moiety.

3. Diagnosis

The present invention is also related to methods of diagnosing conditions associated with altered expression of GPBP. Altered expression of GPBP in a sample may be diagnosed by contacting a sample with an antibody that specifically binds to GPBP, measuring the binding, and comparing the binding to a control. Altered expression of GPBP may be identified by a difference in the binding of the antibody to the sample and the control.

a. Cancer

A condition associated with altered expression of GPBP is cancer. GPBP may be overexpressed in tumors since GPBP-regulated promoters are important in cell growth and differentiation. As discussed above, vasculin as reported by Bijnens et al. is identical to human GPBP, except for a 60 nucleotide exon that is missing in vasculin. An NCBI expression profile search of vasculin shows that GPBP (vasculin) is overexpressed in lung neuroendocrine tumors and inflamed endothelial cells in vascular and colon tissue. Differential expression analysis indicates that GPBP is also overexpressed in certain tumor cells (data not shown). Furthermore, the Examples herein show that GPBP is overexpressed in HeLa cells, which is a very metastatic tumor.

b. Atherogenesis

Another condition associated with altered expression of GPBP is atherogenesis. Bijnens et al. disclose that vasculin is involved in atherogenesis. As discussed above, vasculin as reported by Bijnens et al., is identical to human GPBP except for a 60 nucleotide exon that is missing in vasculin.

4. Nanostructures

The present invention is also related to the use of GPMP polypeptides for stabilizing secondary DNA structures. DNA and DNA-protein complexes are emerging as powerful tools in nanotechnology. DNA nanostructures have been constructed as nanomachines, nanoswitches, nanosensors, scaffolds and for barcodes for commercial and security purposes. The DNA nanostructures may be based on specific patterns of secondary structures based on base sequence. However, the stabilities of DNA secondary structures are affected by local environment, including temperature, ionic environment, and the presence of neighboring sites with the potential to form secondary structures. Regulating DNA secondary structure may also be used in producing replicable nanomachines. For example, complex folded or branched DNA does not readily self-replicate, however, GPBP may be used to regulate secondary and tertiary structures that allow DNA to be cloned, for example, by using the polymerase chain reaction.

The present invention has multiple aspects, illustrated by the following non-limiting examples.

EXAMPLE 1

Molecular Cloning of the Mouse G+C-Rich Promoter Binding Protein mGPBP

The murine ADA gene has an archetypal G+C-rich promoter that contains multiple Sp1 binding sites and a non-canonical TATAAA-like element TAAAAAA. Neither the Sp1 binding sites nor the TAAAAAA sequence are required for basal or enhancer-activated promoter function (Ackerman et al, 1993, Hsu et al., submitted). Instead, the minimal self-sufficient promoter element (MSPE) within the murine ADA gene promoter had previously been shown to reside within a 48 bp element "C" which displays an imperfect dyad sequence symmetry (FIG. 1 of Ackerman et al., 1993). Moreover, Electrophoretic Mobility Shift Assays (EMSA) coupled with DMS footprinting had revealed that a nuclear protein(s) could bind to this element (Ackerman et al., 1993). Many other G+C-rich promoters also contain elements with similar secondary structure-forming potential around their transcription initiation sites (Ackerman et al., 1993). We previously demonstrated that there are nuclear protein-binding sites within the ADA gene's MSPE (Ackerman et al., 1993). This observation led us to attempt the cloning and characterization of the nuclear protein responsible for directing the assembly of the RNA polymerase II transcription initiation complex at this promoter.

We used a $^{32}$P-labeled multimerized ADA promoter fragment C (Ackerman et al., 1993) as a probe to screen a λgt11 bacteriophage mouse brain cDNA expression library for cloned proteins that bind to this MSPE. The restriction fragment C was isolated from plasmid, gel-purified and multimerized by ligating end to end in the presence of T4 ligase. Multimers containing 4-5 copies of the fragment were gel-purified, end-labeled with polynucleotide kinase and γ$^{32}$P-ATP and used to screen the expression library according to the method of Singh et al., 1988. Screening with the negative control Sp1 binding consensus motif probe (TGGGCGGGGC) (SEQ ID NO:11) eliminated clones expressing proteins that bind nonspecifically to random G+C rich sequences. Out of 3×10⁷ clones, 2 clones were identified after tertiary screens and these were further examined by subcloning, restriction digestion and sequence analysis.

Sequence analysis of the subcloned cDNA fragments derived from the two clones revealed that one cDNA insert fragment contained an open reading frame (ORF) which shared regions of sequence homology with several known transcription factors. These factors include yeast TFIIFα, which interacts with RNA polymerase II in transcription initiation complex assembly (Aso et al., 1992, Killeen & Greenblatt, 1992); yeast ARS binding factor 1 (yABF-1), which is a known transcription factor involved in DNA replication initiation in yeast (Biswas et al., 1990, Martens & Brandl, 1994); mouse high mobility group-1-like Structure Specific Recognition Protein 1 (SSRP1), which apparently binds to DNA through structural recognition (Shirakata et al., 1991, Bruhn et al. 1992) and participates in both transcription activation (Dyer et al., 1998, Spencer et al., 1999) and elongation (Orphanides et al., 1999); and helicases, which can unwind double-stranded DNA for transcription and replication (recently reviewed by van Brabant et al., 2000).

Based on our expectations of the properties of the gene sought, this fragment was deemed to be a good candidate clone and was used to generate 2 full-length cDNA clones, 3.0 and 3.5 kb in size, by 3' and 5' rapid amplification of cDNA ends (RACE). RACE was performed using marathon-ready mouse brain cDNA templates and Advantage® cDNA PCR kit manufacturer (Clontech) according to recommended protocols. For the 5' RACE, the primary PCR reaction used primer 5'-CAGGCTGGAGCAAAGTCATGCTGCGCC-3' (SEQ ID NO:7) with the AP1 primer and the nested PCR reaction used primer 5'-AGGTCCAGTCTCTCCAACT-CAGTGAAAC-3' (SEQ ID NO:8) and the AP2 primer. For the 3' RACE, the primary PCR reaction used primer 5'-CT-GATCTGTGACTTCAAGTTTGGACC-3' (SEQ ID NO:9) with the AP1 primer and the nested PCR reaction used primer 5'-TGACGATGTGTGAAGGAGATCCTCACAGC-3' (SEQ ID NO:10) with the AP2 primer. The entire cDNA sequence of the 3,451-bp clone, including the deduced 493 amino acid sequence encoded by the 1,479 bp ORF, and the 815 bp 3'UTR, is shown in FIG. 1A. This cloned gene was named the murine G+C-rich Promoter Binding Protein (mGPBP) gene.

EXAMPLE 2

The mGPBP Transcript is Ubiquitously Expressed as 2 mGPBP Species Differing in 3'-Polyadenylation Site Utilization Because G+C-rich promoters control practically all housekeeping genes, which are essential for cell survival, we predicted that if mGPBP is critical for transcription of these genes, it would be ubiquitously expressed. The full-length mGPBP cDNA sequence was labeled and used as a probe to determine the tissue distribution and mRNA sizes of the gene in a Northern blot analysis.

Mouse Multiple Tissue Northern (MTN™) Blots (Clontech) were hybridized with murine GPBP cDNA probes and washed under standard conditions (Sambrook et al., 1989). The probes used were gel-purified, individually cloned mGPBP cDNA restriction fragments. The blots used were stripped as previously described (Gum, R. et al., submitted) and reprobed with a β-actin cDNA probe as a loading control. All probes were synthesized by the random hexanucleotide-priming method (Feinberg and Vogelstein, 1984) and purified using a Bio-Gel P-30 column (BIO-RAD).

The results (FIG. 2A) showed that the gene is highly expressed in all mouse tissues analyzed as 2 mRNA species sized at 3.0 and 3.5 kb, respectively. Because we had two 3' RACE products that differed in size by ~500 bp, and each product contained consensus AATAAA polyadenylation signaling motifs located appropriately upstream of the poly-A tracts, we surmised that the 3.0 and 3.5 kb mRNA species may represent the same RNA with different polyadenylation site utilization. This prediction was confirmed when we cloned out a 2.0 kb fragment from the 5' end and a 350 bp fragment from the 3' end of the longer cDNA clone and used them as probes, respectively, on the same Northern blot which was stripped between each hybridization experiment. The results (FIG. 2B) revealed that the 5' probe hybridized with both the 3.0 and 3.5 kb mRNA species, whereas the 3' probe hybridized only with the 3.5 kb mRNA species. These observations indicate that both these cross-hybridizing mRNAs contain the entire ORF of the mGPBP gene and differ only in their choice of 3' polyadenylation site usage.

EXAMPLE 3

Expression of Recombinant mGPBP

The murine GPBP cDNA's ORF sequence was inserted downstream of the hexa-histidine tag sequence of pET28a (Novagen) to yield the bacterial expression vector pETmG-PBP that can synthesize recombinant his-tagged mGPBP upon IPTG induction. The bacterial expression vector used to synthesize recombinant GST-mGPBP fusion protein was generated by inserting the mGPBP cDNA's ORF downstream of the glutathione S-transferase (GST) cDNA sequence in plasmid pGEX-4T-1 (Pharmacia) to yield construct pGEX-mGPBP. These bacterial expression constructs were transformed into E. coli strains BL21/DE3 and BL21 for the production of recombinant mGPBP, respectively. The eukaryotic mGPBP expression vector pCDNA-mGPBP was generated by inserting the mGPBP cDNA's ORF into the pCDNA3 expression vector (Invitrogen). The hemagglutinin antigen (HA)-tagged (Field, 1988[2]) mGPBP eukaryotic expression construct pCDNAHA-mGPBP was generated by inserting the (HA) tag coding sequence upstream of, and in frame with, the mGPBP cDNA's ORF in pCDNA-mGPBP.

The 1,479 bp ORF of the mGPBP cDNA clone was inserted downstream of the IPTG-inducible promoter as an in-frame histidine-tagged fusion protein encoding sequence in the PET28a bacterial expression plasmid. The resultant pETmGPBP plasmid was introduced into the E. coli BL21/DE3 strain host for recombinant mGPBP synthesis. Cell lysates from IPTG-induced and IPTG-uninduced transformed BL21 cells were prepared and analyzed by SDS polyacrylamide gel electrophoresis (PAGE) and Coomassie Blue staining. Cell lysates from IPTG-induced cells displayed a prominent 66 kD protein band that was absent from IPTG-uninduced cells (FIG. 3A, lanes 3&2, respectively). The 1,479 bp ORF of the mGPBP cDNA clone was also inserted into pCDNA3 (Invitrogen), a eukaryotic expression vector. Expression of the ORF in reticulocyte lysates also resulted in the synthesis of a novel 66 kD protein.

Recombinant His-tagged mGPBP was purified under native conditions using Qiagen's Ni-NTA agarose following the manufacturer's protocol with minor modifications. After incubation of bacterial lysate with a 50% Ni-NTA agarose slurry at 4° C. for 2 hours, the resin-bound protein was eluted from the agarose matrix and the protein fractions containing the purified protein were then pooled and dialyzed twice for 60 minutes each, first against 500 ml of dialysis buffer (20 mM Tris-HCl, pH7.5, 50 mM KCl, 10 mM $MgCl_2$, 10 µM $ZnSO_4$, 1 mM EDTA, 20% glycerol, 0.5 mM DTT, 0.2 mM PMSF) containing 0.25M NaCl, and then against 500 ml of the same dialysis buffer without NaCl. The his-mGPBP fusion protein purified by $Ni^{++}$ resin affinity column chromatography and SDS-PAGE was found to be >95% pure as revealed by SDS-PAGE and Coomassie Blue staining analysis (FIG. 3A, lane 4).

EXAMPLE 4

Inhibitory Effect of UTR

The presence of all or part of the 1.15 kb 5' UTR in the mGPBP mRNA had an inhibitory effect in the translation of this mRNA in both expression systems: bacteria (FIG. 3) and reticulocyte lysates (data not shown). However, only a single 66 kd translation product was produced irrespective of the size of the 5' UTR present in the mRNA (data not shown). The 3' UTR of the GPBP mRNA contains multiple TAAAT repeats (FIG. 1A) that are reportedly involved in mRNA turnover control (Shaw and Kamen, 1986). The presence of either the long or short 3'UTR also had no effect on the size of the translation product generated from the mRNA using either prokaryotic or mammalian in vitro translation systems (data not shown).

EXAMPLE 5

Production of Antibodies to mGPBP

Recombinant mGPBP (His-tagged) used to raise anti-mG-PBP antiserum was purified under denaturing conditions using Ni-NTA agarose (Qiagen) following the vendor's instruction and then isolated as a single excised band following electrophoresis in 8.5% sodium dodecyl sulfate-polyacrylamide gel (SDS-PAGE). The recovered mGPBP protein was concentrated by using ULTRAFREE®-MC 10,000NMWL filter units (Millipore).

Purified his-mGPBP was used to raise rabbit polyclonal antiserum against mGPBP. Immunization was performed at the Immunological Resource Center at the University of Illinois. Antibodies from the antiserum were purified by using the ImmunoPure® (A/G) IgG purification kit (Pierce), as suggested by the manufacturer. Eluted antibodies were combined, dialyzed against PBS and concentrated with centrifugal filtration units (Millipore).

The mGPBP antiserum was shown by Western blot analyses to be immunoreactive against mGPBP in either IPTG-induced pETmGPBP carrying BL21 cell lysate or purified mGPBP preparations (FIG. 3A, lanes 7&8, respectively) and showed no cross-reactivity with BL21 bacterial proteins (FIG. 3A, lane 6).

EXAMPLE 6

Expression Pattern of mGPBP

The anti-mGPBP antiserum was used to examine the presence of GPBP in several human and mouse cell lines. Cells were lysed in RIPA buffer (25 mM Tris pH 8.2, 50 mM NaCl, 0.5% Nonidet P40, 0.5% sodium deoxcholate, 0.1% SDS, 0.1% sodium azide) containing 1 mM PMSF, 10 µg/ml of aprotinin and 10 µg/ml of leupeptin. Cell lysates were incubated on ice for 15 minutes and centrifuged at 12,000×g for 10 min. at 4° C. The protein concentration of the cleared lysates was determined using the BioRad protein assay kit. Equal amounts of protein per lane were analyzed in 8.5% SDS-PAGE. Western blotting was carried out using Amersham PVDF membranes according to the vendor's recommendations.

All of the cell lysates analyzed by Western blotting using the anti-mGPBP antiserum as probe revealed a prominent 66 kD band (FIG. 3B). Since the cells used were of both mouse (FIG. 3B, lanes 2&5) and human (FIG. 3B, lanes 1, 3, 4&6) origin, the results indicate that our anti-mGPBP antiserum is immunoreactive with both mouse and human GPBP. This conclusion was confirmed by subsequent Western blot analyses performed on purified and recombinant human GPBP, which is encoded by a similarly sized ORF in our full-length human GPBP cDNA clone (FIG. 8). Thus the ORF within our full-length mGPBP cDNA clone does encode a 66 kD protein and the translation product of that ORF in either bacterial or mammalian cells was immunoreactive to our anti-mGPBP antiserum. Tissue distribution analysis confirmed that GPBP is present in all mammalian tissues and cells examined to date, as predicted for a candidate critical regulator of housekeeping gene transcription.

EXAMPLE 7

Recombinant mGPBP can Bind Specifically to the MSPE of the Mouse ADA Gene

The DNA binding capability of mGPBP was examined directly in EMSAs using either the multimerized fragment C' with imperfect dyad symmetry (see FIG. 5 of Ackerman et al., 1993) or the 236 bp murine ADA gene promoter as probe. The probes were isolated as restriction fragments from plasmids and radiolabeled with $\alpha^{32}$P-dCTP using Klenow fragment. Electrophoretic mobility shift assays were performed as previously described (Christy and Nathans, 1989) with minor modifications. Binding-reaction mixtures containing purified bacterially expressed recombinant proteins were prepared in binding buffer (10 mM Tris-HCl pH7.5, 60 mM KCl, 5 mM $MgCl_2$, 0.5 mM DTT, 0.1 mM EDTA, 10 µM $ZnCl_2$, 0.05% NP-40, 12-15% glycerol) containing 0.5 µg of poly-dI/dC (20 µl total volume). After the binding reaction mixtures had been incubated for 10 minutes at room temperature, the radiolabeled probe was added for an additional 20 minutes of incubation at room temperature. The mixture was then separated in 4% (acrylamide/bis-acrylamide-29:1) non-denaturing polyacrylamide gel containing 1× TBE buffer.

The assay results are shown in FIG. 4. In panel A, the labeled DNA probe used consisted of 4 tandem-repeat copies of fragment C' (4C') that had been end-ligated. Purified recombinant mGPBP bound specifically to this probe and retarded probe electrophoretic mobility (FIG. 4A, lanes 1 &2). This binding was specifically competed out by adding excess unlabeled probes (lanes 3 & 4), but not by adding similar amounts of unlabeled E2F binding motif (lanes 5 & 6) or a 200 bp plasmid sequence (lanes 7 & 8). As indicated in panel B, a single copy of this fragment C' in the context of the labeled 236 bp mouse ADA gene promoter also bound to purified recombinant mGPBP (lanes 1 & 2). This binding was competed out by excess unlabeled probe (lanes 3 & 4) or by excess amounts of the unlabeled tandem repeated C' fragment (4C') probe used in FIG. 4A (lanes 5 & 6). Again, this binding was not competed out by similar excess amounts of unlabeled E2F binding sequence (lanes 7 & 8) or the 200 bp plasmid sequences (lanes 9 & 10). In similar gel mobility shift assays using the 200 bp plasmid sequences as probe, mGPBP was unable to bind to and retard the mobility of this nonspecific DNA probe (data not shown). These results demonstrate that recombinant mGPBP can bind specifically to the 48 bp MSPE located within the 236 bp murine ADA gene promoter.

EXAMPLE 8

GPBP is a Nuclear Protein

Since cellular transcription factors all function within the cell nucleus, we used indirect immunofluorescence to examine the cellular localization of the GPBP. This was accomplished by using protein-A affinity-purified antibodies derived from our anti-mGPBP antiserum αN-80 to immunostain fixed and permeablized human HeLa cells, which were then counter-stained with DAPI to locate the nuclei.

$5 \times 10^5$ Hela cells were plated in DMEM containing 10% fetal calf serum in 60 mm dishes containing glass coverslips and incubated at 37° C. overnight. The following day the cells were transfected with 5 μg of either the pCDNAHA-mGPBP expression construct or the pCDNA-HA control vector using a calcium phosphate transfection protocol as described previously (Ackerman et al., 1993). The hemagglutinin antigen (HA)-tagged (Field, 1988[2]) mGPBP eukaryotic expression construct pCDNAHA-mGPBP was generated by inserting the (HA) tag coding sequence upstream of, and in frame with, the mGPBP cDNA's ORF in pCDNA-mGPBP. Sixteen hours after transfection, the cells were rinsed extensively with PBS, treated with fresh medium and incubated for an additional 48 hours. The cells were then rinsed with PBS and fixed with 4% paraformaldehyde for 30 minutes at room temperature. After fixation the cells were permeablized with 0.2% Triton X-100/PBS for 5 minutes, rinsed and stained with either mGPBP antibodies, or preimmune antisera derived antibodies that had been purified by binding to protein A-conjugated beads, or antibody against HA (2 μg/ml) at 37° C. for 1 hour. After washing 4 times (5 minutes/wash) with PBS the cells were stained with either rabbit or mouse fluorescein-conjugated secondary antibodies (1:200 dilution) (Amersham) at 37° C. for an additional hour. The coverslips were then washed extensively, mounted in antifade solution (Vector Lab) containing 0.25 μg/ml DAPI to counterstain the nuclei and photographed using a Zeiss Axiovert microscope with an attached Princeton Instruments CCD camera.

The anti-mGPBP signal was nuclear-localized (FIG. 5A). In control experiments using protein-A affinity-purified antibodies derived from pre-immune antiserum as a probe, immuno-reactive signals were negligible even upon prolonged photographic exposure (FIG. 5B). The nuclear localization of GPBP was confirmed by directly transfecting the mGPBP expression vector into human HeLa cells and immunostaining for mGPBP using our anti-mGPBP antibodies (FIG. 5C, top panel). Definitive proof that our recombinant mGPBP was nuclear-localized was provided by transfecting an mGPBP-HA-tag fusion protein expression vector into human HeLa cells and immunostaining for the tagged protein with anti-HA antibodies (FIG. 5C bottom panel). These in situ immunohistochemical analyses demonstrated that both the endogenous human GPBP and the exogenous cDNA-encoded recombinant mGPBP could translocate into the cell nucleus.

EXAMPLE 9

In Vitro complex formation of GPBP with Multiple Key Factors that Participate in Mammalian RNA-Polymerase II Transcription Initiation Complex Assembly If GPBP binding to the G+C-rich promoter's MSPE can lead to the assembly of the transcription initiation complex at that location, GPBP should be able to interact with one or more transcription factors that normally participate in transcription initiation complex formation. This expectation was tested by assaying whether immobilized recombinant GST-mGPBP fusion protein could complex with various nuclear transcription factors of the RNA polymerase II transcription initiation complex, present in nuclear extracts.

The bacterial expression vector used to synthesize recombinant GST-mGPBP fusion protein was generated by inserting the mGPBP cDNA's ORF downstream of the glutathione S-transferase (GST) cDNA sequence in plasmid pGEX-4T-1 (Pharmacia) to yield construct pGEX-mGPBP. This bacterial expression constructs were transformed into E. coli strains BL21 for the production of recombinant mGPBP. The GST-mGPBP fusion protein was purified according to a published protocol (Guan and Dixon, 1991) with minor modifications. After IPTG induction, the bacterial cells were pelleted and resuspended in PBS containing 10 mMDTT, 0.5 mM PMSF and 2 μg/ml each of leupeptin, pepstain A, and antipain, sonicated, and subsequently treated with 1/10 volume of 10% Triton X-100. The GST-fusion protein in the supernatant was then purified by one step affinity chromatography using glutathione-sepharose beads (Pharmacia) according to the vendor's recommendations.

Nuclear extracts were prepared as previously described (Berger and Kimmel, 1987) with minor modifications. Mouse C1-1D Cells were collected and washed with 10 volumes of PBS once. The cells were then suspended in 5 volumes of cold buffer A (10 mM Hepes-KOH pH 7.9, mM KCL, 1.5 mM $MgCl_2$, 0.1 mM EGTA, 0.5 mM DTT, 0.5 mM PMSF, 2 μg/ml each of antipain, leupeptin, and pepstain) and incubated on ice for 15 minutes. Cells were lysed using 20 strokes of a Dounce homogenizer (B pestle), and a further 2-5 strokes in the presence of 0.3-0.4% Nonidet-P40 (NP-40). The lysed cells were centrifuged at 1,300×g for 10 minutes. The pelleted nuclei were washed thrice with buffer A without NP-40, centrifuged again as above, and resuspended in 1-2 volumes of cold buffer B (10 mM HEPES-KOH pH7.9, 0.1 mM EGTA, 0.5 mM DTT, 400 mM NaCl, 5% glycerol, 0.5 mM PMSF) and incubated on ice for 60 minutes. The solution was then centrifuged at 48,000×g for 1 hour. The supernatant was dialyzed twice against 500 ml of dialysis buffer (20 mM HEPES-KOH pH7.9, 75 mM NaCl, 0.1 mM EDTA, 0.5 mM DTT, 20% glycerol, 0.5 mM PMSF) for 1 hr., cleared by centrifugation in a microcentrifuge for 15 min.

Recombinant mGPBP fused in-frame to the GST tag was immobilized by binding the GST moiety to glutathione covalently linked to beads. 1-5 μg of the fusion protein was incubated with 100 μl of a 50% slurry of glutathione-Sepharose beads (Pharmacia) for 1 hour at 4° C. The protein-bound beads were collected and washed three times with PBS buffer. The beads were then re-suspended in binding buffer (20 mM Hepes-KOH pH7.9, 75 mM NaCl, 0.1 mM EDTA, 0.5 mM DTT, 20% glycerol, 0.5 mM PMSF) (Hayes et al., 1998). About 1/60 of the beads were subjected to 8.5% SDS-PAGE to confirm that GST proteins were bound to the beads. Mouse C1-1D nuclear extract proteins were then allowed to bind to the bead-immobilized mGPBP by incubating the rest of the beads with 100 μg of C1-1D cell nuclear extract on a rotator overnight at 4° C. The beads were collected and washed three times with washing buffer (20 mM Tris-HCl, pH8.0, 150 mM NaCl, 1 mM EDTA, and 0.1-0.3% NP-40). The bound proteins were eluted with SDS-sample buffer and subjected to 4-20% SDS-PAGE. Western blotting was then carried out on the gels. Both the unbound proteins in the supernatant and the proteins that remained bound to the immobilized mGPBP after extensive washing were then analyzed by Western blotting using antibodies against various transcription factors as probes.

Figure 6:
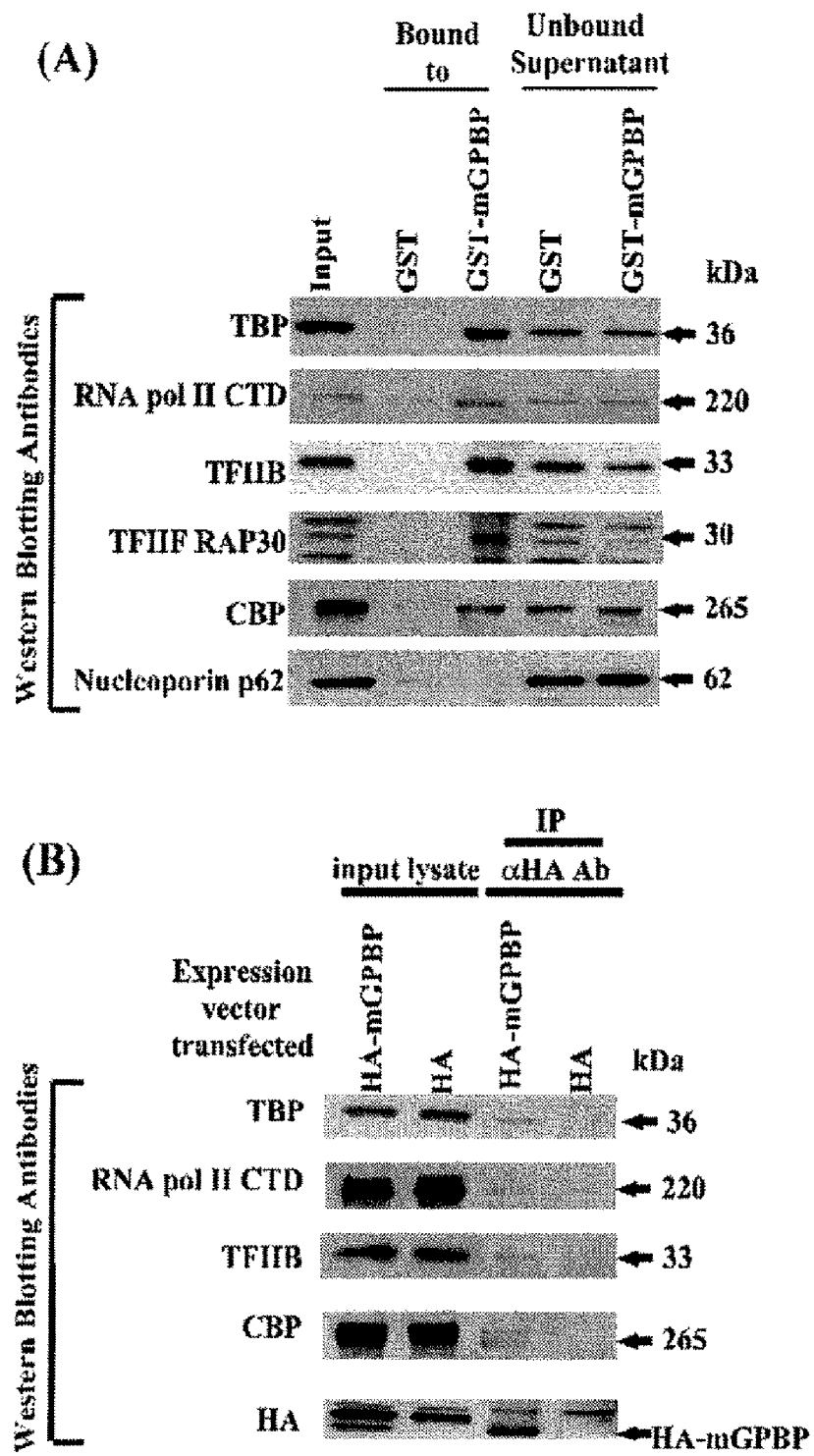
FIG. 6 shows that the mGPBP can complex with multiple transcription initiation complex assembly specific factors. (A) Mouse C1-1D cell nuclear extract proteins were allowed to bind to bead immobilized GST-mGPBP fusion proteins. The various proteins, including the starting nuclear extract (Input), proteins that bind to bead immobilized GST or GST-mGPBP fusion proteins (Bound to), and proteins that did not bind to bead immobilized GST or GST-mGPBP fusion proteins (Unbound Supernatant) were analyzed by Western blotting. The antibodies used to probe these blots were raised against TBP, The C-terminal domain of RNA polymerase II (RNA pol II CTD), Transcription Fraction IIB (TFIIB), Transcription Fraction IIF RAP30 subunit (TFIIF RAP30), P300/CAAT Binding Protein (CBP), and the negative control antibodies against the nuclear envelope protein Nucleoporin p62. The estimated molecular weight of proteins in each band (in Kd) based on electrophoretic mobility in comparison to protein size markers were shown on the right by arrows. (B) In vivo binding of mGPBP was determined by immuno-coprecipitation analyses of cell lysates. Western blot analyses showed C1-1D cell lysate proteins after the cells were transfected with expression vectors that express either the HA-tag (HA) alone, or the HA-tag fused to mGPBP (HA-mGPBP), without immunoprecipitation (input lysate), or after immunoprecipitation with antibodies against the HA-tag (IP αHA Ab). The antibodies raised against TBP, RNA pol II CTD, TFIIB, CBP, or HA-tag were used as probes as indicated in each blot. The estimated molecular weight of proteins in each band (in Kd) based on electrophoretic mobility in comparison to protein size markers are shown on by arrows. The migration location of the HA-mGPBP fusion protein is also shown on the right of the panel with an arrow.

The results showed that known transcription initiation complex factors such as the TATA-binding Protein (TBP), Transcription Fraction IIB (TFIIB), Transcription Fraction IIF (TFIIF RAP30), and RNA polymerase II (RNA pol II CTD), as well as the transcription factor P300/CAAT Binding Protein (CBP), all complexed with the immobilized recombinant mGPBP (FIG. 6A). None of these same proteins complexed with only the GST tag immobilized onto the same glutathione beads, and the unbound supernatant recovered from both binding assays showed that the same proteins were similarly present in both binding assays. The nuclear membrane protein nucleoporin p62, which does not participate in transcription initiation complex formation, showed no affinity to either immobilized mGPGP or GST (FIG. 6A). These in vitro results demonstrate that mGPBP can complex specifically with several key transcription initiation factors.

EXAMPLE 10

In Vivo Complex Formation of GPBP with Multiple Key Factors that Participate in Mammalian RNA-Polymerase II Transcription Initiation Complex Assembly To examine whether the in vitro complexing of GPBP with transcription factors also occurs in vivo, we performed a co-immunoprecipitation experiment using an HA-tagged mGPBP expression construct in mouse C1-1D cells. The hemagglutinin antigen (HA)-tagged (Field, 1988[2]) mGPBP eukaryotic expression construct pCDNAHA-mGPBP was generated by inserting the (HA) tag coding sequence upstream of, and in frame with, the mGPBP cDNA's ORF in pCDNA-mGPBP. Anti-HA antibodies were used to immunoprecipitate nuclear extract proteins derived from the transfected cells. As a control, nuclear extract from cells transfected with the HA expression vector containing no GPBP-encoding sequences underwent a similar immunoprecipitation procedure.

Cells were collected by centrifugation in PBS 48 hours after DNA transfection. Cells from each 100-mm dish were treated with 60 µl of lysis buffer containing 20 mM HEPES pH7.9, 400 mM NaCl, 1 mM EDTA, 0.1% NP-40, 1 mM DTT, 0.5 mM PMSF, 10% glycerol and 1.5 µl of protease inhibitors cocktail (Sigma) (Hayes et al., 1998). Cell lysates were incubated for 30 minutes at 4° C., and centrifuged at 13,000×g for 10 min. at 4° C. The supernatant from each 100-mm dish was treated with 300 µl of lysis buffer without NaCl, and incubated with agarose bead-bound anti-HA antibody (Santa Cruz) overnight at 4° C. The beads were pelleted and washed 3-4 times with 1 ml of buffer W (20 mM Tris-HCl, pH8.0, 100 mM NaCl, 0.1-0.3% Np-40, 1 mM EDTA, 1 mM DTT, 0.5 mM PMSF).

The proteins that co-immunoprecipitated with anti-HA antibodies were then analyzed by Western blotting with a 4%-20% precast SDS-PAGE (BioWittaker Molecular Applications) using antibodies against TBP, TFIIB, CBP, and RNA polymerase II as probes. The antibodies used were anti-HA monoclonal antibodies (clone 12CA5, Boehringer Mannheim); anti-RNAPII CTD (RNA polymerase II C-terminal Domain) monoclonal antibodies (Promega); anti-HA monoclonal antibodies conjugated with agarose, rabbit anti-TFIIB polyclonal antibodies C-18, rabbit anti-TFIIF RAP30 polyclonal antibodies C-17, anti-TBP monoclonal antibodies 58C9, rabbit anti-CBP polyclonal antibodies A-22 and WT rabbit polyclonal antibodies 180 (Santa Cruz); and anti-Nucleoporin p62 monoclonal antibodies clone 53 (Transduction Laboratories).

A portion of the respective nuclear extracts prior to treatment with anti-HA antibodies (input lysate, FIG. 6B) were shown by Western blotting to contain all the requisite proteins. None of the nuclear transcription factors of interest co-immunoprecipitated with the HA tag alone. In contrast, TBP, TFIIB, CBP, RNA polymerase II (FIG. 6B) and TFIIF RAP30 (data not shown) all co-immunoprecipitated with the HA-tagged mGPBP. These results demonstrate that GPBP does complex with these transcription factors both in vitro and in vivo.

EXAMPLE 11

Transcription from the Mouse ADA Gene's G+C-Rich Promoter Requires GPBP

To examine whether our cloned mGPBP could trans-activate a luciferase reporter gene controlled by the mouse ADA gene's G+C-rich promoter, we co-transfected both mouse C1-1D cells and human 293 cells with a constant amount of the reporter construct and increasing amounts of the mGPBP expression vector.

Monolayer cultures of murine C1-1D LM (TK⁻) fibroblast cells derived from bone marrow stromal cells of a (C57B1/6J×C3H/HeJ) F1 mouse, and human embryonic kidney (HEK) 293 cells were maintained in 10% fetal calf serum in DMEM (Dulbecco's Modified Eagle's Medium). For each 60-mm plate of C1-1D or 293 cells, 0.2 µg of the luciferase reporter gene under the control of the murine ADA gene promoter was co-transfected with various amounts of murine GPBP-expression plasmid (pCDNA-mGPBP) using Lipofectamine Plus (for 3 hours), as suggested by the manufacturer (Gibco BRL). The total amount of plasmid used per plate was brought up to 2 µg with the empty pCDNA3 vector. The transfected cells were washed with PBS and then cultured in 10% FCS in DMEM medium for 24-36 hours prior to being harvested for reporter gene expression analyses. All transfection assays were repeated at least 3 times using different DNA preparations. The luciferase activities of the transfected cell lysates were measured using a luciferase assay system (Promega) and the VICTO²™ Multilabel Counter (Wallac). The obtained values were then normalized according to the protein concentrations. (Bio-Rad Protein Assay). For both C1-1D and 293 cell lines, reporter gene expression increased linearly with the amount of the mGPBP expression vector added in a dose dependent manner (FIG. 7A).

To address the question of whether GPBP is specifically required for transcription directed by the murine ADA gene's G+C-rich promoter, we performed in vitro transcription assays. In-vitro transcription reactions were carried out as previously described (Dignam et al., 1983) with minor modifications. Supercoiled template DNA was purified by banding twice in centrifuged CsCl gradients (Sambrook et al., 1989). The templates used consist of G-less cassette reporters which were either without a promoter (construct $pC_2AT$-Sawadogo and Roeder, 1985), with the adenovirus major late promoter (construct $PMLC_2AT$, Sawadogo and Roeder, 1985) or with the murine ADA gene promoter ($pmADAPC_2AT$-generated by PCR). Transcription reaction mixtures (25 µl total volume) containing 8 mM HEPES (pH 7.9), 40 mM KCl, 6 mM $MgCl_2$, 0.08 mM EDTA, 0.2 mM DTT, 8% glycerol, 30 units of RNase Ti, 100 ng template DNA, 9-10 µg HeLa nuclear extract (Promega), and different amounts of antibodies and purified recombinant protein were incubated at 30° C. for 10 minutes prior to the addition of 0.2 mM of ATP, CTP, and GTP to 0.2 mM each, UTP to 8 nM, 3'-O-Methyl-guanosine 5'-triphosphate (Pharmacia) to 0.05 mM, and $\alpha$-$^{32}$P-UTP (800 Ci/mmole) to 1 µM. The reaction mixtures were then incubated for 1 hour at 30° C. The reactions were stopped by the addition of 175 µl of stop solution (0.3 M Tris-HCl, pH7.4, 0.3 M sodium acetate, 0.5% SDS, 2 mM EDTA, 25 µg/ml tRNA) and an extraction control 200 bp end-labeled DNA fragment. The reaction solutions were extracted twice with phenol/chloroform/isoamyl alcohol (25:24:1, v/v/v). The nucleic acids in the reaction were ethanol precipitated, air-dried and dissolved in 4 µl of Nuclease-Free water. An equal volume of loading dye (98% formamide, 10 mM EDTA, 0.1% xylene cyanol, 0.1% bromophenol blue) was added to the in vitro transcribed RNA solution. These RNA solutions were then heated at 90° C. for 10 minutes and electrophoresed in a 6% denaturing (7 M urea) polyacrylamide gel containing 0.5×TBE buffer. The amounts of radiolabeled transcript and extraction control bands were then quantified using a Phosphorimager (Molecular Dynamic).

The transcription assays were performed in the presence of HeLa cell nuclear extracts from which GPBP had been incrementally sequestered by the addition of increasing amounts of anti-mGPBP antibodies that can cross-react with human GPBP. Recovery of the reporter transcripts from the transcription reaction mix was monitored using a labeled carrier control DNA. FIG. 7B shows a representative result from experiments that were repeated three or more times. In the presence of increasing amounts of anti-mGPBP antibodies, there was a corresponding decrease in transcript production (FIG. 7B, lanes 4-9). When increasing amounts of purified recombinant mGPBP were added back to the antibody-treated nuclear extract, the observed antibody-induced suppression of reporter gene transcription was correspondingly reversed (FIG. 6B, lanes 10 and 11). Control experiments revealed that pre-immune serum antibodies had no suppressive effect on reporter gene transcription (FIG. 7B, lanes 3, 2, &1). The suppressive effect of anti-mGPBP antibodies on transcription was observed only when the reporter gene was under the control of the G+C-rich promoter. Transcription of the same reporter gene under the control of the adenovirus-major late gene's TATAAA-box dependent promoter was not diminished by the immuno-sequestering of GPBP in the nuclear extract (FIG. 7B, lanes 12-15). Quantifying all the labeled bands in several experiments using a phosphorimager allowed us to demonstrate the reproducibility of the results as summarized in FIG. 7C. These results indicate that although GPBP is required for transcription directed by the ADA gene's G+C-rich promoter, it is not required for transcription directed by the adenovirus Major late gene's classical TATAAA-box dependent promoter.

EXAMPLE 12

The G+C-Rich TopoIIa Gene Promoter Binds Specifically to mGPBP

To examine whether mGPBP is a general requisite G+C-rich promoter-dependent transcription factor, we also examined whether this protein can bind to other G+C-rich promoters, especially one that contains a consensus TATA box and G+C-rich rich regions that display no obvious homology to the murine ADA gene promoter, as in the case of the human topoisomerase IIα promoter (FIG. 9A). EMSAs using the labeled TopoIIa promoter as the probe showed that the TopoIIa gene promoter can also bind specifically to purified recombinant mGPBP in the absence of any other mammalian transcription factors, This binding can be competed out by either excess unlabeled probe or excess unlabelled fragments containing four copies of the murine Ada gene MSPE but not by excess copies of a 100-bp fragment derived from the pUC2H vector, which does not adopt non-B form DNA structures under negative supercoiling conditions.

EXAMPLE 13

Transcription Initiation can be Only Partially Suppressed by Immunosequestration of mGPBP In HeLa cell nuclear extract-dependent in vitro transcription assays, we demonstrated that transcription initiation at the murine Ada gene promoter required the presence of GPBP whereas transcription initiation at a consensus TATA box-dependent adenovirus major late gene promoter did not. Since this TopoIIa gene promoter binds specifically to mGPBP but contains a canonical TATA box, we also examined how this promoter functioned when the GPBP in the nuclear extract was sequestered by immunoabsorption. Sequestering of GPBP in the HeLa nuclear extract with anti-GPBP antibodies under conditions that totally suppresses transcription initiated by the murine Ada gene promoter showed only a partial suppressive effect on transcription initiation by the TopoIIa gene promoter (FIG. 9C). This suppression can also be fully reverse by the addition of purified recombinant mGPBP to the nuclear extract. The results in FIG. 9 thus demonstrated that mGPBP can indeed bind to other G+C-rich promoters and that the presence of a canonical TATA box rendered the TopoIIa gene promoter only partially dependent on GPBP for transcription initiation, in contrast to the total dependence of the murine Ada gene promoter on GPBP for transcription in the absence of such a canonical element.

REFERENCES

Ackerman, S. L., Minden, A. G., Williams, G. T., Bobonis, C., and Yeung, C-Y. (1991). Functional significance of an overlapping consensus binding motif for Sp1 and Zif268 in the murine adenosine deaminase promoter. Proc. Natl. Acad. Sci. USA 88: 7523-7527

Ackerman, S. L., Minden, A. G., and Yeung, C-Y. (1993). The minimal self-sufficient element in a murine G+C rich promoter is a large element with imperfect dyad symmetry. Proc. Natl. Acad. Sci. USA 90: 11865-11869

Arias, J. A., and Dynan, W. S. (1989). Promoter-dependent transcription by RNA polymerase II using immobilized enzyme complexes. J. Biol. Chem. 264: 3223-3229

Aronow, B., Lattier, D., Silbiger, R., Dusing, M., Hutton, J., Jones, G., Stock, J., McNeish, J., Potter, S., Witte, D., and Wiginton, D. 1989. Evidence for a complex regulatory array in the first intron of the human adenosine deaminase gene. Genes Dev. 3: 1384-1400

Aso T, Vasavada H A, Kawaguchi T, Germino F J, Ganguly S, Kitajima S, Weissman S M, Yasukochi Y. (1992). Characterization of cDNA for the large subunit of the transcription initiation factor TFIIF. Nature 355: 461-4

Biswas E E, Stefanec M J, Biswas S B. (1990). Molecular cloning of a gene encoding an ARS binding factor from the yeast *Saccharomyces cerevisiae*. Proc Natl Acad Sci U S A. 87:6689-92

Blake, M. C., Jamboum R. C., Swick, A. G., Kahn, J. W., and Azizkhan, J. C. (1990). Transcriptional initiation is controlled by upstream GC-box interactions in a TATAA-less promoter. Mol. Cell. Biol. 10: 6632-6641

Bradford, M. M. (1976). A rapid and sensitive method for the quantitation of microgram quantities of protein utilizing the principle of protein-dye binding. Anal. Biochem. 72: 248-254

Bruhn S L, Pil P M, Essigmann J M, Housman D E, Lippard S J. (1992) Isolation and characterization of human cDNA clones encoding a high mobility group box protein that recognizes structural distortions to DNA caused by binding of the anticancer agent cisplatin. Proc Natl Acad Sci USA 89:2307-11

Buratowski, S., Hahn., S., Guarente, L., and Sharp, P. A. (1989). Five intermediate complexes in transcription initiation by RNA polymerase II. Cell 56: 549-561

Chan H M, La Thangue N B. (2001). p300/CBP proteins: HATs for transcriptional bridges and scaffolds. J Cell Sci. 114:2363-73

Dyer, M. A., Hayes, P. J., and Baron, M. H. (1998). The HMG domain protein SSRP1/PREIIBF is involved in activation of the hauman embryonic beta-like globin gene. Mol. Cell. Biol. 18:2617-28

Feinberg, A. P., and Vogelstein, B. (1984). A technique for radiolabeling DNA restriction endonuclease fragments to high specific activity. Anal. Biochem. 137: 266-267, (Addendum to Anal. Biochem. 132: 6-13.)

Fujita (Ausubel, F. M., Brent, R., Kingston, R. E., Moore, D. M., Deidman, J. G., Smith, J. A., and Struhl, K, Seidman, J. G. (1987). Current Protocols in Molecular Biology. New York, Greene Publishing Associates and Wiley-Interscience Hsu, L-C., Minden, A., Gum, R., Ackerman, S., Abedinpour, F., Dayn, A., Mirkin, S. M., Ross, S. R., and Yeung, C-Y. (2001). The murine ADA gene has a G+C rich promoter that is operationally distinct from a TATAA box or initiator element dependent promoter. (Submitted)

Ingolia, D. E., Al-Ubaidi, M. R., Yeung, C.-Y., Bigo, H. A., Wright, D. A., and Kellems, R. E. (1986). Molecular cloning of the murine adenosine deaminase gene from a genetically enriched source: identification and characterization of the promoter region. Mol. Cell. Biol. 6: 4458-4466

Innis, J. W., Moore, D. J., Kash, S. F., Ramamurthy, V., Sawadogo, M., and Kellems, R. E. (1991). The murine adenosine deaminase promoter requires an atypical TATA box which binds transcription factor IID and transcriptional activity is stimulated by multiple upstream Sp1 binding sites. J. Biol. Chem. 266: 21765-21772, Killeen M T, Greenblatt J F. (1992): The general transcription factor RAP30 binds to RNA polymerase II and prevents it from binding nonspecifically to DNA. Mol Cell Biol 12:30-7

Martens, J. A., and Brandl, C. J. (1994). GCN4p activation of the yeast TRP3 gene is enhanced by ABF1p and uses a suboptimal TATA element. J. Biol. Chem. 269: 15661-15667.

Means, A. L., and Farnham, P. J. (1990a). Transcription initiation from the dihydrofolate reductase promoter is positioned by HIP1 binding at the initiation site. Mol Cell Biol. 10: 653-61

Means, A. L., and Farnham, P. J. (1990b). Sequences downstream of the transcription initiation site modulate the activity of the murine dihydrofolate reductase promoter. Mol Cell Biol. 10:1390-8

Orphanides, G., W.-H. Wu, W. S. Lane, M. Hampsey, and D. Reinberg. (1999). The chromatin-specific transcription elongation factor FACT comprises human SPT16 and SSRP1 proteins. Nature 400:284-288.

Rauth, S., Yang, K.-G., Seibold, A. M., Ingolia, D. E., Ross, S. R., and Yeung, C-Y. (1990). GC-rich murine adenosine deaminase gene promoter supports diverse tissue-specific gene expression. Som. Cell Molec. Genet. 16: 129-141, Saiki, R. K., Gelfand, D. H., Stoffel, S., Scharf, S. J., Higuchi, R., Horn, G. T., Mullis, K. B., Erlich, H. A. (1988). Primer-directed enzymatic amplification of DNA with a thermostable DNA polymerase. Science 239: 487-491

Sambrook, J., Fritsch, E. F., and Maniatis, T. (1989). In: Molecular Cloning: A Laboratory Manual. 2nd ed., Cold Spring Harbor, N. Y., Cold Spring Harbor Laboratory Press Sanger, F., Nicklen, S., and Coulson, A. R. (1977). DNA sequencing with chain-terminating inhibitors. Proc Natl. Acad. Sci. USA. 74: 5463-5467

Sawadogo, M., and Roeder, R. G. (1985). Factors involved in specific transcription by human RNA polymerase II: analysis by a rapid and quantitative in vitro assay. Proc. Natl. Acad. Sci. USA 82:4394-8

Shaw, G., and Kamen, R. (1986). A Conserved AU sequence from the 3' untranslated region on GM-CSF mRNA mediates selective mRNA degradation. Cell 46:659-667

Shirakata, M., Huppi, K., Usuda, S., Okazaki, K., Yoshida, K. & Sakano, H. (1991) HMG1-related DNA-binding protein isolated with V-(D)-J recombination signal probes. Mol. Cell. Biol. 11, 4528-4536

Singh H, LeBowitz J H, Baldwin A S Jr, Sharp P A. (1988) Molecular cloning of an enhancer binding protein: isolation by screening of an expression library with a recognition site DNA. Cell 52: 415-23

Southern, E. M. (1975). Detection of specific sequences among DNA fragments separated by gel electrophoresis. J. Mol. Biol. 98: 503-517, Spencer, J. A., Baron, M. H., and Olson, E. N. (1999). Cooperative Transcriptional Activation by Serum Response Factor and the High Mobility Group Protein SSRP1. J. Biol. Chem. 274: 15686-15693

Trembley, J. H., Hu, D., Hsu, L-C., Yeung, C-Y., Slaughter, C., Reinberg, D., Lahti, J. M., and Kidd, V. J. (2002) PITSLRE p110 Protein Kinases Associate with Transcription Complexes and Effect their Activity. In Press, J. Biol. Chem.

Van Brabant, van Brabant A J, Stan R, Ellis N A. (2000): DNA helicases, genomic instability, and human genetic disease. Annu Rev Genomics Hum Genet.; 1:409-59.

Yeung, C.-Y., Ingolia, D. E., Bobonis, C., Dunbar, B. S., Riser, M. E., Siciliano, M. J., and Kellems, R. E. (1983). Selective overproduction of adenosine deaminase in cultured mouse cells. J. Biol. Chem. 258: 8338-8345

The invention claimed is:

1. An isolated DNA encoding G+C-rich Promoter Binding Protein (GPBP) polypeptide, said polypeptide comprising a sequence selected from the group consisting of SEQ ID NO:2 and SEQ ID NO:4.

2. The DNA of claim 1, wherein said DNA comprises a sequence selected from the group consisting of SEQ ID NO:1 and SEQ ID NO:3.

3. A vector which comprises the DNA of claim 1 or claim 2, wherein said DNA is operatively linked to a control region.

4. The vector of claim 3, wherein said vector is an expression vector.

5. An isolated host cell comprising the vector of claim 3.

6. An isolated host cell comprising the vector of claim 4.

* * * * *